United States Patent
DiMarchi et al.

(10) Patent No.: US 7,557,183 B2
(45) Date of Patent: Jul. 7, 2009

(54) POLYETHYLENE GLYCOL LINKED GLP-1 COMPOUNDS

(75) Inventors: Richard Dennis DiMarchi, Carmel, IN (US); Wolfgang Glaesner, Indianapolis, IN (US); Rohn Lee Millican, Jr., Indianapolis, IN (US); Andrew Mark Vick, Fishers, IN (US); Lianshan Zhang, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 261 days.

(21) Appl. No.: 10/548,328

(22) PCT Filed: Mar. 19, 2004

(86) PCT No.: PCT/US2004/006082

§ 371 (c)(1),
(2), (4) Date: Apr. 12, 2007

(87) PCT Pub. No.: WO2004/093823

PCT Pub. Date: Nov. 4, 2004

(65) Prior Publication Data

US 2008/0113905 A1    May 15, 2008

Related U.S. Application Data

(60) Provisional application No. 60/456,081, filed on Mar. 19, 2003.

(51) Int. Cl.
*A61K 38/26* (2006.01)
*A61K 38/00* (2006.01)

(52) U.S. Cl. .......................... 530/308; 530/324; 514/12

(58) Field of Classification Search ....................... None
See application file for complete search history.

(56) References Cited

U.S. PATENT DOCUMENTS

| 5,705,483 | A | 1/1998 | Galloway et al. |
| 6,924,264 | B1 | 8/2005 | Prickett et al. |
| 7,238,663 | B2 * | 7/2007 | DeFelippis et al. ............ 514/12 |

FOREIGN PATENT DOCUMENTS

| WO | WO 98/08871 | 3/1998 |
| WO | WO 00/66629 | 9/2000 |
| WO | WO 03/018516 | 3/2003 |
| WO | WO 03/058203 | 3/2003 |
| WO | WO 03/040309 | 5/2003 |
| WO | WO 2004/022004 | 3/2004 |
| WO | WO 2005/058954 | 6/2005 |

OTHER PUBLICATIONS

Goke, R. et al., "Exendin-4 Is a High Potency Agonist and Truncated Exendin—(9-39)-amide an Antagonist at the Glucagon-like Peptide 1-(7-36)-amide Receptor of Insulin-secreting β-Cells." The Journal of Biological Chemistry, vol. 268, No. 26, pp. 19650-19655, 1993.

* cited by examiner

*Primary Examiner*—Suzanne M. Noakes
(74) *Attorney, Agent, or Firm*—Andrea M. Castetter; Gregory A. Cox

(57) ABSTRACT

The invention provides GLP-1 compounds coupled to at least one polyethylene glycol molecule or derivative thereof, resulting in a biologically active peptide with an extended half-life and a slower clearance when compared to that of unPEGylated peptide. These PEGylated GLP-1 compounds and compositions are useful in treating diabetes, obesity, irritable bowel syndrome and other conditions that would be benefited by lowering plasma glucose, inhibiting gastric and/or intestinal motility and inhibiting gastric and/or intestinal emptying, or inhibiting food intake.

10 Claims, No Drawings

POLYETHYLENE GLYCOL LINKED GLP-1 COMPOUNDS

This is the national phase application, under 35 USC 371, for PCT/US04/006082 filed Mar. 19, 2004, which claims the priority of U.S. provisional application No. 60/456,081 filed Mar. 19, 2003.

FIELD OF THE INVENTION

The present invention relates to GLP-1 compounds covalently attached to one or more molecules of polyethylene glycol or a derivative thereof, and related compositions and methods useful in treating conditions or disorders benefited by lowering blood glucose, decreasing food intake, decreasing gastric or intestinal emptying, or decreasing gastric or intestinal motility.

BACKGROUND OF THE INVENTION

Glucagon-like peptide-1 (GLP-1) induces numerous biological effects such as stimulating insulin secretion, inhibiting glucagon secretion, inhibiting gastric emptying, inhibiting gastric motility or intestinal motility, enhancing glucose utilization, and inducing weight loss. GLP-1 may further act to prevent the pancreatic β-cell deterioration that occurs as non-insulin dependent diabetes mellitus (NIDDM) progresses. A significant characteristic of GLP-1 is its ability to stimulate insulin secretion without the associated risk of hypoglycemia that is seen when using insulin therapy or some types of oral therapies that act by increasing insulin expression.

The usefulness of therapy involving GLP-1 peptides has been limited by the fact that GLP-1(1-37) is poorly active, and the two naturally occurring truncated peptides, GLP-1(7-37) OH and GLP-1(7-36)$NH_2$, are rapidly cleared in vivo and have extremely short in vivo half lives. It is known that endogenously produced dipeptidyl-peptidase IV (DPP-IV) inactivates circulating GLP-1 peptides by removing the N-terminal histidine and alanine residues and is a major reason for the short in vivo half-life.

Various approaches have been undertaken to extend the elimination half-life of a GLP-1 peptide or reduce clearance of the peptide from the body while maintaining a biological activity. U.S. Pat. No. 5,705,483 teaches GLP-1 peptide analogs made resistant to DPP-IV degradation by the incorporation of modifications at the N-terminus of the peptide. An alternative approach for extending the half-life of GLP-1 peptides is derivatization, wherein large acyl groups that prevent DPP-IV from accessing the N-terminus of the peptide are attached to various amino acids of GLP-1 (See International Application No. PCT/DK97/00340, filed Aug. 22, 1997 entitled "GLP-1 Derivatives," which claims the benefit of DK Provisional Application Nos. 0931/96 filed Aug. 30, 1996, 1259/96 filed Nov. 8, 1996 and 1470/96 filed Dec. 20, 1996).

Particular GLP-1 analogs are described in U.S. patent application Ser. No. 60/346,474 filed Jan. 8, 2002, and U.S. patent application Ser. No, 60/405,097 filed Aug. 21, 2002, now International Application No. PCT/US03/058203, filed Jan. 3, 2003, all entitled "Extended Glucagon-Like Peptide-1 Analogs" and are incorporated herein in their entirety. These applications describe analogs of GLP-1(7-37)OH wherein various amino acids, when added to the C-terminus, yield GLP-1 peptide analogs with an extended half-life and reduced clearance than that of the native molecule. Furthermore, GLP-1 logs with increased potency are described in U.S. patent application Seri. No. 60/314,573 filed Aug. 23, 2001, now International Application No. PCT/US02/21325, filed Aug. 14, 2002, entitled "Glucagon-Like Peptide-1 Analogs" (incorporated herein). Exendin-4 can act at the GLP-1 receptor in vitro on certain cell types including insulin-secreting cells. [Goke, et al., *J. Biol. Chem.*, (1993)268:19650-19655]. Particular PEGylated exendin and exendin agonist molecules are described in International Application Number PCT/US00/11814 (incorporated herein in its entirety).

While various approaches have resulted in GLP-1 compounds with a longer half-life or greater potency than that of native GLP-1, additional approaches that could be used either alone or in combination with known approaches are needed to further decrease GLP-1 compound clearance and increase GLP-1 compound half-life thereby optimizing its ability to be useful as a therapeutic that can be administered a minimum number of times during a prolonged period of time. Covalent attachment of one or more molecules of polyethylene glycol to a small, biologically active peptide such as GLP-1 or exendin-4 poses the risk of introducing adverse characteristics such as instability to the molecule and reduction in bioactivity so severe as to make the molecule unsuitable for use as a therapeutic. The present invention; however, is based on the finding that covalent attachment of one or more molecules of PEG to particular residues of a GLP-1 compound results in a biologically active, PEGylated GLP-1 compound with an extended half-life and reduced clearance when compared to that of native GLP-1 or $Val_8$-GLP-1 (or native exendin-4 for modified exendin-4 peptides of the invention).

The PEGylated GLP-1 compounds of the invention have greater usefulness as a therapeutic as well as greater convenience of use than native GLP-1 because they retain all or a portion of a biological activity of native GLP-1 yet have an enhanced half-life and/or reduced clearance when compared to that of the native GLP-1 compound or to that of $Val_8$-GLP-1(7-37)OH. GLP-1(7-37) has a serum half-life of only 3 to 5 minutes. GLP-1(7-36) amide has a time action of about 50 minutes when administered subcutaneously. Even GLP-1 analogs and derivatives that are resistant to endogenous protease cleavage, do not have half-lives long enough to avoid repeated administrations over a 24 hour period. PEGylated GLP-1 compounds of the invention may have a half-life in excess of 24 hours allowing for fewer administrations of the PEGylated GLP-1 compound while maintaining a high blood level of the compound over a prolonged period of time. Such PEGylated GLP-1 compounds may be used therapeutically to treat subjects with disorders including, but not limited to, diabetes, obesity, gastric and/or intestinal motility abnormalities, and gastric and/or intestinal emptying abnormalities with a particular advantage being that the PEGylated GLP-1 compounds of the invention require fewer doses during a 24 hour period, increasing both the convenience to a subject in need of such therapy and the likelihood of subject's compliance with dosing requirements.

SUMMARY OF THE INVENTION

The invention described herein provides GLP-1 compounds covalently attached to one or more molecules of polyethylene glycol (PEG), or a derivative thereof wherein each PEG is attached at a Cys or Lys amino acid or the carboxy terminus of the peptide, resulting in PEGylated GLP-1 compounds with an elimination half-life of at least one hour, preferably at least 3, 5, 7, 10, 15, 20 hours and most preferably at least 24 hours. The PEGylated GLP-1 compounds of the present invention preferably have a clearance value of 200 ml/h/kg or less, more preferably 180, 150, 120, 100, 80, 60 ml/h/kg or less and most preferably less than 50, 40 or 20 ml/h/kg.

One embodiment of the invention is a PEGylated GLP-1 compound comprising the amino acid sequence of GLP-1(7-37)OH as shown in SEQ ID NO: 1 with a PEG molecule covalently attached at 3, 2 or 1 of the residues selected from the group consisting of $Lys_{26}$, $Lys_{34}$ and $Gly_{37}$:

```
                                                  (SEQ ID NO: 1)
⁷His-Ala-Glu-¹⁰Gly-Thr-Phe-Thr-Ser-¹⁵Asp-Val-Ser-

Ser-Tyr-²⁰Leu-Glu-Gly-Gln-Ala-²⁵Ala-Lys-Glu-Phe-

Ile-³⁰Ala-Trp-Leu-Val-Lys-³⁵Gly-Arg-³⁷Gly.
```

Another embodiment of the invention is a PEGylated GLP-1 compound comprising the amino acid sequence of GLP-1(7-36)$NH_2$ as shown in SEQ ID NO: 2 with a PEG molecule covalently attached at 3, 2 or 1 of the residues selected from the group consisting of $Lys_{26}$, $Lys_{34}$ and $Arg_{36}$:

```
                                                  (SEQ ID NO: 2)
⁷His-Ala-Glu-¹⁰Gly-Thr-Phe-Thr-Ser-¹⁵Asp-Val-Ser-

Ser-Tyr-²⁰Leu-Glu-Gly-Gln-Ala-²⁵Ala-Lys-Glu-Phe-

Ile-³⁰Ala-Trp-Leu-Val-Lys-³⁵Gly-Arg.
```

Another embodiment of the present invention is a PEGylated GLP-1 compound comprising the amino acid sequence of Formula I (SEQ ID NO: 3)

```
Formula 1
                                                  (SEQ ID NO: 3)
Xaa₇-Xaa₈-Glu-Gly-Xaa₁₁-Xaa₁₂-Thr-Ser-Asp-Xaa₁₆-

Ser-Xaa₁₈-Xaa₁₉-Xaa₂₀-Glu-Xaa₂₂-Xaa₂₃-Xaa₂₄-Xaa₂₅-

Xaa₂₆-Xaa₂₇-Phe-Ile-Xaa₃₀-Trp-Leu-Xaa₃₃-Xaa₃₄-

Xaa₃₅-Xaa₃₆-Xaa₃₇
``` wherein:
$Xaa_7$ is: L-histidine, D-histidine, desamino-histidine, 2-amino-histidine, β-hydroxy-histidine,
homohistidine, α-fluoromethyl-histidine, or α-methyl-histidine;
$Xaa_8$ is: Ala, Gly, Val, Leu, Ile, Ser, or Thr;
$Xaa_{11}$ is: Thr or Cys;
$Xaa_{12}$ is: Phe, Trp, Tyr, or Cys;
$Xaa_{16}$ is: Val, Trp, Ile, Leu, Phe, Tyr, or Cys;
$Xaa_{18}$ is: Ser, Trp, Tyr, Phe, Lys, Ile, Leu, Val;
$Xaa_{19}$ is: Tyr, Trp, or Phe;
$Xaa_{20}$ is: Leu, Phe, Tyr, or Trp;
$Xaa_{22}$ is: Gly, Glu, Asp, Lys, or Cys;
$Xaa_{23}$ is: Gln or Cys;
$Xaa_{24}$ is: Ala or Cys;
$Xaa_{25}$ is: Ala, Val, Ile, Leu, or Cys;
$Xaa_{26}$ is: Lys or Cys;
$Xaa_{27}$ is: Glu, Ile, Ala, or Cys;
$Xaa_{30}$ is: Ala, Glu, or Cys
$Xaa_{33}$ is: Val or Ile;
$Xaa_{34}$ is: Lys or Cys;
$Xaa_{35}$ is: Gly or Cys;
$Xaa_{36}$ is: Arg or Cys;
$Xaa_{37}$ is: Gly, His, Cys, $NH_2$, or is absent;
and wherein:

2 or 1 of the Cys residues are covalently attached to a PEG molecule, or 3, 2 or 1 of the Lys residues are covalently attached to a PEG molecule, or the carboxy-terminal amino acid is covalently attached to a PEG molecule; and provided that there are 2, 1 or 0 Cys in the molecule.

Another embodiment of the present invention is a PEGylated GLP-1 compound comprising the amino acid sequence of Formula II (SEQ ID NO: 4):

```
Formula II
                                                  (SEQ ID NO: 4)
Xaa₇-Xaa₈-Glu-Gly-Xaa₁₁-Xaa₁₂-Thr-Ser-Asp-Xaa₁₆-

Ser-Xaa₁₈-Tyr-Leu-Glu-Xaa₂₂-Xaa₂₃-Xaa₂₄-Xaa₂₅-

Xaa₂₆-Xaa₂₇-Phe-Ile-Xaa₃₀-Trp-Leu-Xaa₃₃-Xaa₃₄-

Xaa₃₅-Xaa₃₆-Xaa₃₇
``` wherein:
$Xaa_7$ is: L-histidine, D-histidine, desamino-histidine, 2-amino-histidine, β-hydroxy-histidine,
homohistidine, α-fluoromethyl-histidine, or α-methyl-histidine;
$Xaa_8$ is: Gly, Ala, Val, Leu, Ile, Ser, or Thr;
$Xaa_{11}$ is: Thr or Cys;
$Xaa_{12}$ is: Phe, or Cys
$Xaa_{16}$ is: Val, Phe, Tyr, Trp, or Cys;
$Xaa_{18}$ is: Ser, Tyr, Trp, Phe, Lys, Ile, Leu, or Val;
$Xaa_{19}$ is: Tyr or Phe;
$Xaa_{22}$ is: Gly, Glu, Asp, Lys, or Cys;
$Xaa_{23}$ is: Gln or Cys;
$Xaa_{24}$ is: Ala or Cys;
$Xaa_{25}$ is: Ala, Val, Ile, Leu, or Cys;
$Xaa_{26}$ is: Lys or Cys;
$Xaa_{27}$ is: Glu or Cys;
$Xaa_{30}$ is: Ala or Cys;
$Xaa_{33}$ is: Val or Ile;
$Xaa_{34}$ is: Lys or Cys;
$Xaa_{35}$ is: Gly or Cys;
$Xaa_{36}$ is: Arg or Cys; and
$Xaa_{37}$ is: Gly, Cys, $NH_2$, or is absent, and wherein:

2 or 1 of the Cys residues are covalently attached to a PEG molecule, or 3, 2 or 1 of the Lys residues are covalently attached to a PEG molecule, or the carboxy-terminal amino acid is covalently attached to a PEG molecule;

and provided that there are 2, 1 or 0 Cys in the molecule.

Another embodiment of the present invention is a PEGylated GLP-1 compound comprising the amino acid sequence of Formula III (SEQ ID NO: 5)

Formula III
(SEQ ID NO: 5)
Xaa$_7$-Xaa$_8$-Glu-Gly-Xaa$_{11}$-Xaa$_{12}$-Thr-Ser-Asp-Xaa$_{16}$-

Ser-Xaa$_{18}$-Xaa$_{19}$-Xaa$_{20}$-Glu-Xaa$_{22}$-Xaa$_{23}$-Xaa$_{24}$-Xaa$_{25}$-

Xaa$_{26}$-Xaa$_{27}$-Phe-Ile-Xaa$_{30}$-Trp-Leu-Xaa$_{33}$-Xaa$_{34}$-

Xaa$_{35}$-Xaa$_{36}$-Xaa$_{37}$-Xaa$_{38}$-Xaa$_{39}$-Xaa$_{40}$-Xaa$_{41}$-Xaa$_{42}$-

Xaa$_{43}$-Xaa$_{44}$-Xaa$_{45}$-Xaa$_{46}$-Xaa$_{47}$-Xaa$_{48}$-Xaa$_{49}$-Xaa$_{50}$ wherein:
Xaa$_7$ is: L-histidine, D-histidine, desamino-histidine, 2-amino-histidine, β-hydroxy-histidine, homohistidine, α-fluoromethyl-histidine, or α-methyl-histidine;
Xaa$_8$ is: Ala, Gly, Val, Leu, Ile, Ser, or Thr;
Xaa$_{11}$ is: Thr or Cys;
Xaa$_{12}$ is: Phe, Trp, Tyr, or Cys;
Xaa$_{16}$ is: Val, Trp, Ile, Leu, Phe, Tyr, or Cys;
Xaa$_{18}$ is: Ser, Trp, Tyr, Phe, Lys, Ile, Leu, or Val;
Xaa$_{19}$ is: Tyr, Trp, or Phe;
Xaa$_{20}$ is: Leu, Phe, Tyr, or Trp;
Xaa$_{22}$ is: Gly, Glu, Asp, Lys, or Cys;
Xaa$_{23}$ is: Gln or Cys;
Xaa$_{24}$ is: Ala or Cys;
Xaa$_{25}$ is: Ala, Val, Ile, Leu, or Cys;
Xaa$_{26}$ is: Lys or Cys;
Xaa$_{27}$ is: Glu, Ile, Ala, or Cys;
Xaa$_{30}$ is: Ala, Glu, or Cys;
Xaa$_{33}$ is: Val or Ile;
Xaa$_{34}$ is: Lys, Asp, Arg, Glu, or Cys;
Xaa$_{35}$ is: Gly or Cys;
Xaa$_{36}$ is: Gly, Pro, Arg, or Cys;
Xaa$_{37}$ is: Gly, Pro, Ser, or Cys;
Xaa$_{38}$ is: Ser, Pro, His, or Cys;
Xaa$_{39}$ is: Ser, Arg, Thr, Trp, Lys, or Cys;
Xaa$_{40}$ is: Ser, Gly, or Cys;
Xaa$_{41}$ is: Ala, Asp, Arg, Glu, Lys, Gly, or Cys;
Xaa$_{42}$ is: Pro, Ala, Cys, or NH$_2$, or is absent;
Xaa$_{43}$ is: Pro, Ala, Cys, NH$_2$, or is absent;
Xaa$_{44}$ is: Pro, Ala, Arg, Lys, His, Cys, NH$_2$, or is absent;
Xaa$_{45}$ is: Ser, His, Pro, Lys, Arg, Gly, Cys, NH$_2$ or is absent;
Xaa$_{46}$ is: His, Ser, Arg, Lys, Pro, Gly, Cys, NH$_2$ or is absent; and
Xaa$_{47}$ is: His, Ser, Arg, Lys, Cys, NH$_2$ or is absent;
Xaa$_{48}$ is: Gly, His, Cys, NH$_2$, or is absent;
Xaa$_{49}$ is: Pro, His, Cys, NH$_2$, or is absent;
Xaa$_{50}$ is: Ser, His, Cys, Ser-NH$_2$, His-NH$_2$, Cys-NH$_2$, or is absent;

and wherein:

2 or 1 of the Cys residues are covalently attached to a PEG molecule, or 3, 2 or 1 of the Lys residues are covalently attached to a PEG molecule, or the carboxy-terminal amino acid is covalently attached to a PEG molecule;

and provided that if Xaa$_{42}$, Xaa$_{43}$, Xaa$_{44}$, Xaa$_{45}$, Xaa$_{46}$, Xaa$_{47}$, Xaa$_{48}$ or Xaa$_{49}$ is absent each amino acid downstream is absent; and provided that there are 2, 1 or 0 Cys in the molecule.

Another embodiment of the present invention is a PEGylated GLP-1 compound comprising the amino acid sequence of Formula IV (SEQ ID NO:6)

Formula IV
(SEQ ID NO: 6)
Xaa$_7$-Xaa$_8$-Glu-Gly-Xaa$_{11}$-Xaa$_{12}$-Thr-Ser-Asp-Xaa$_{16}$-

Ser-Xaa$_{18}$-Xaa$_{19}$-Xaa$_{20}$-Glu-Xaa$_{22}$-Xaa$_{23}$-Xaa$_{24}$-Xaa$_{25}$-

Xaa$_{26}$-Xaa$_{27}$-Phe-Ile-Xaa$_{30}$-Trp-Leu-Xaa$_{33}$-Xaa$_{34}$-

Xaa$_{35}$-Xaa$_{36}$-Xaa$_{37}$-Xaa$_{38}$-Xaa$_{39}$-Xaa$_{40}$-Xaa$_{41}$-Xaa$_{42}$-

Xaa$_{43}$-Xaa$_{44}$-Xaa$_{45}$-Xaa$_{46}$-Xaa$_{47}$ wherein:
Xaa$_7$ is: L-histidine, D-histidine, desamino-histidine, 2-amino-histidine, β-hydroxy-histidine, homohistidine, α-fluoromethyl-histidine, or α-methyl-histidine;
Xaa$_8$ is: Ala, Gly, Val, Leu, Ile, Ser, or Thr;
Xaa$_{11}$ is: Thr or Cys
Xaa$_{12}$ is: Phe, Trp, Tyr, or Cys;
Xaa$_{16}$ is: Val, Trp, Ile, Leu, Phe, Tyr, or Cys;
Xaa$_{18}$ is: Ser, Trp, Tyr, Phe, Lys, Ile, Leu, Val;
Xaa$_{19}$ is: Tyr, Trp, or Phe;
Xaa$_{20}$ is: Leu, Phe, Tyr, or Trp;
Xaa$_{22}$ is: Gly, Glu, Asp, Lys or Cys;
Xaa$_{23}$ is: Gln or Cys;
Xaa$_{24}$ is: Ala or Cys;
Xaa$_{25}$ is: Ala, Val, Ile, Leu, or Cys;
Xaa$_{26}$ is: Lys or Cys;
Xaa$_{27}$ is: Glu, Ile, Ala, or Cys;
Xaa$_{30}$ is: Ala, Glu or Cys
Xaa$_{33}$ is: Val or Ile;
Xaa$_{34}$ is: Lys, Asp, Arg, Glu or Cys;
Xaa$_{35}$ is: Gly or Cys;
Xaa$_{36}$ is: Gly, Pro, Arg or Cys;
Xaa$_{37}$ is: Gly, Pro, Ser or Cys;
Xaa$_{38}$ is: Ser, Pro, His or Cys;
Xaa$_{39}$ is: Ser, Arg, Thr, Trp, Lys or Cys;
Xaa$_{40}$ is: Ser, Gly, or Cys;
Xaa$_{41}$ is: Ala, Asp, Arg, Glu, Lys, Gly, or Cys;
Xaa$_{42}$ is: Pro, Ala, Cys, NH$_2$, or is absent;
Xaa$_{43}$ is: Pro, Ala, Cys, NH$_2$, or is absent;
Xaa$_{44}$ is: Pro, Ala, Arg, Lys, His, Cys, NH$_2$, or is absent;
Xaa$_{45}$ is: Ser, His, Pro, Lys, Arg, Cys, NH$_2$ or is absent;
Xaa$_{46}$ is: His, Ser, Arg, Lys, Cys, NH$_2$ or is absent; and
Xaa$_{47}$ is: His, Ser, Arg, Lys, Cys, NH$_2$ or is absent;

and wherein:

2 or 1 of the Cys residues are covalently attached to a PEG molecule, or 3, 2 or 1 of the Lys residues are covalently attached to a PEG molecule, or the carboxy-terminal amino acid is covalently attached to a PEG molecule;

and provided that if Xaa$_{42}$, Xaa$_{43}$, Xaa$_{44}$, Xaa$_{45}$ or Xaa$_{46}$ is absent each amino acid downstream is absent; and provided that there are 2, 1 or 0 Cys in the molecule.

Another embodiment of the present invention is a PEGylated GLP-1 compound comprising the amino acid sequence of Formula V (SEQ ID NO:7)

Formula V
(SEQ ID NO: 7)
Xaa$_7$-Xaa$_8$-Glu-Gly-Xaa$_{11}$-Xaa$_{12}$-Thr-Ser-Asp-Xaa$_{16}$-

Ser-Ser-Tyr-Lys-Glu-Xaa$_{22}$-Xaa$_{23}$-Xaa$_{24}$-Xaa$_{25}$-Xaa$_{26}$-

-continued

Xaa$_{27}$-Phe-Ile-Xaa$_{30}$-Trp-Leu-Xaa$_{33}$-Xaa$_{34}$-Xaa$_{35}$-

Xaa$_{36}$-Xaa$_{37}$-Xaa$_{38}$-Xaa$_{39}$-Xaa$_{40}$-Xaa$_{41}$-Xaa$_{42}$-Xaa$_{43}$-

Xaa$_{44}$-Xaa$_{45}$-Xaa$_{46}$-Xaa$_{47}$ wherein:
Xaa$_7$ is: L-histidine, D-histidine, desamino-histidine, 2-amino-histidine, β-hydroxy-histidine,
homohistidine, α-fluoromethyl-histidine, or α-methyl-histidine;
Xaa$_8$ is: Gly, Val, Leu, Ile, Ser, or Thr;
Xaa$_{11}$ is: Thr or Cys;
Xaa$_{12}$ is: Phe or Cys;
Xaa$_{16}$ is: Val, Trp, Ile, Leu, Phe, Tyr, or Cys;
Xaa$_{22}$ is: Gly, Glu, Asp, Lys, or Cys;
Xaa$_{23}$ is: Gln or Cys;
Xaa$_{24}$ is: Ala or Cys;
Xaa$_{25}$ is: Ala, Val, Ile, Leu, or Cys;
Xaa$_{26}$ is: Lys or Cys;
Xaa$_{27}$ is: Glu or Cys;
Xaa$_{30}$ is: Ala or Cys;
Xaa$_{33}$ is: Val or Ile;
Xaa$_{34}$ is: Lys, Asp, Arg, Glu, or Cys;
Xaa$_{35}$ is: Gly or Cys;
Xaa$_{36}$ is: Gly, Pro, Arg, or Cys;
Xaa$_{37}$ is: Gly, Pro, Ser, or Cys;
Xaa$_{38}$ is: Ser, Pro, His, or Cys;
Xaa$_{39}$ is: Ser, Arg, Thr, Trp, Lys, or Cys;
Xaa$_{40}$ is: Ser, Gly, or Cys;
Xaa$_{41}$ is: Ala, Asp, Arg, Glu, Lys, Gly, or Cys;
Xaa$_{42}$ is: Pro, Ala, or Cys;
Xaa$_{43}$ is: Pro, Ala, or Cys;
Xaa$_{44}$ is: Pro, Ala, Arg, Lys, His, Cys, NH$_2$, or is absent;
Xaa$_{45}$ is: Ser, His, Pro, Lys, Arg, Cys, NH$_2$ or is absent;
Xaa$_{46}$ is: His, Ser, Arg, Lys, Cys, NH$_2$ or is absent; and
Xaa$_{47}$ is: His, Ser, Arg, Lys, Cys, NH$_2$ or is absent;

and wherein:

2 or 1 of the Cys residues are covalently attached to a PEG molecule, or 3, 2 or 1 of the Lys residues are covalently attached to a PEG molecule, or the carboxy-terminal amino acid is covalently attached to a PEG molecule;

and provided that if Xaa$_{44}$, Xaa$_{45}$, Xaa$_{46}$, or Xaa$_{47}$ is absent each amino acid downstream is absent; and provided that there are 2, 1 or 0 Cys in the molecule.

Another embodiment of the present invention is a PEGylated GLP-1 compound comprising the amino acid sequence of Formula VI (SEQ ID NO:8)

Formula VI
(SEQ ID NO: 8)
Xaa$_7$-Xaa$_8$-Glu-Gly-Xaa$_{11}$-Xaa$_{12}$-Thr-Ser-Asp-Xaa$_{16}$-

Ser-Ser-Tyr-Lys-Glu-Xaa$_{22}$-Xaa$_{23}$-Xaa$_{24}$-Xaa$_{25}$-Xaa$_{26}$-

Xaa$_{27}$-Phe-Ile-Xaa$_{30}$-Trp-Leu-Xaa$_{33}$-Xaa$_{34}$-Xaa$_{35}$-

Xaa$_{36}$-Xaa$_{37}$-Xaa$_{38}$-Xaa$_{39}$-Xaa$_{40}$-Xaa$_{41}$-Xaa$_{42}$-Xaa$_{43}$-

Xaa$_{44}$-Xaa$_{45}$-Xaa$_{46}$-Xaa$_{47}$ wherein:
Xaa$_7$ is: L-histidine, D-histidine, desamino-histidine, 2-amino-histidine, β-hydroxy-histidine,
homohistidine, α-fluoromethyl-histidine, or α-methyl-histidine;
Xaa$_8$ is: Gly, Val, Leu, Ile, Ser, or Thr;
Xaa$_{11}$ is: Thr or Cys;
Xaa$_{12}$ is: Phe or Cys;
Xaa$_{16}$ is: Val or Cys;
Xaa$_{22}$ is: Gly, Glu, Asp, Lys or Cys;
Xaa$_{23}$ is: Gln or Cys;
Xaa$_{24}$ is: Ala or Cys;
Xaa$_{25}$ is: Ala, Val, Ile, Leu, or Cys;
Xaa$_{26}$ is: Lys or Cys;
Xaa$_{27}$ is: Glu or Cys;
Xaa$_{30}$ is: Ala or Cys;
Xaa$_{33}$ is: Val or Ile;
Xaa$_{34}$ is: Lys or Cys;
Xaa$_{35}$ is: Gly or Cys;
Xaa$_{36}$ is: Gly or Cys;
Xaa$_{37}$ is: Pro or Cys;
Xaa$_{38}$ is: Ser, Pro, His, or Cys;
Xaa$_{39}$ is: Ser, Arg, Thr, Trp, Lys, or Cys;
Xaa$_{40}$ is: Ser, Gly, or Cys;
Xaa$_{41}$ is: Ala, Asp, Arg, Glu, Lys, Gly, or Cys;
Xaa$_{42}$ is: Pro, Ala, or Cys;
Xaa$_{43}$ is: Pro, Ala, or Cys;
Xaa$_{44}$ is: Pro, Ala, Arg, Lys, His, Cys, NH$_2$, or is absent;
Xaa$_{45}$ is: Ser, His, Pro, Lys, Arg, Cys, NH$_2$ or is absent;
Xaa$_{46}$ is: His, Ser, Arg, Lys, Cys, NH$_2$ or is absent; and
Xaa$_{47}$ is: His, Ser, Arg, Lys, Cys, NH$_2$ or is absent;

and wherein:

2 or 1 of the Cys residues are covalently attached to a PEG molecule, or 3, 2 or 1 of the Lys residues are covalently attached to a PEG molecule, or the carboxy-terminal amino acid is covalently attached to a PEG molecule;

provided that if Xaa$_{44}$, Xaa$_{45}$, Xaa$_{46}$, or Xaa$_{47}$ is absent each amino acid downstream is absent and provided that there are 2, 1 or 0 Cys in the molecule.

Another embodiment of the present invention is a PEGylated GLP-1 compound comprising the amino acid sequence of Formula VII (SEQ ID NO:9)

Formula VII
(SEQ ID NO: 9)
His-Ala-Glu-Gly-Thr-Phe-Thr-Ser-Asp-Val-Ser-Ser-

Tyr-Leu-Glu-Gly-Gln-Ala-Ala-Lys-Glu-Phe-Ile-Ala-

Trp-Leu-Val-Lys-Gly-Gly-Pro-Xaa$_{38}$-Xaa$_{39}$-Xaa$_{40}$-

Xaa$_{41}$-Xaa$_{42}$-Xaa$_{43}$-Xaa$_{44}$-Xaa$_{45}$-Xaa$_{46}$-Xaa$_{47}$-Xaa$_{48}$-

Xaa$_{49}$-Xaa$_{50}$

Wherein:

Xaa11 is: Thr or Cys;

Xaa12 is: Phe or Cys;

Xaa16 is: Val or Cys;

Xaa22 is: Gly or Cys;

Xaa23 is: Gln or Cys;

Xaa24 is: Ala or Cys;

Xaa25 is: Ala or Cys;

Xaa26 is: Lys or Cys;

Xaa27 is: Glu or Cys;

Xaa30 is: Ala or Cys;

Xaa34 is: Lys or Cys;

Xaa35 is: Gly or Cys;

Xaa36 is: Gly or Cys;

Xaa37 is: Pro or Cys;

$Xaa_{38}$ is: Ser, Pro, His or Cys;

$Xaa_{39}$ is: Ser, Arg, Thr, Trp, Lys or Cys;

$Xaa_{40}$ is: Ser, Gly or Cys;

$Xaa_{41}$ is: Ala, Asp, Arg, Glu, Lys, Gly or Cys;

$Xaa_{42}$ is: Pro, Ala, Cys, $NH_2$, or is absent;

$Xaa_{43}$ is: Pro, Ala, Cys, $NH_2$, or is absent;

$Xaa_{44}$ is: Pro, Ala, Arg, Lys, His, Cys, $NH_2$, or is absent;

$Xaa_{45}$ is: Ser, His, Pro, Lys, Arg, Gly, Cys, $NH_2$ or is absent;

$Xaa_{46}$ is: His, Ser, Arg, Lys, Pro, Gly, Cys, $NH_2$ or is absent; and $Xaa_{47}$ is: His, Ser, Arg, Lys, Cys, $NH_2$ or is absent;

$Xaa_{48}$ is: Gly, His, Cys, $NH_2$ or is absent;

$Xaa_{49}$ is: Pro, His, Cys, $NH_2$ or is absent; and $Xaa_{50}$ is: Ser, His, Cys, Ser-$NH_2$, His-$NH_2$, Cys-$NH_2$, or is absent;

wherein said GLP-1 compound comprises from one to seven further substitutions and wherein:

2 or 1 of the Cys residues are covalently attached to a PEG molecule, or 3, 2 or 1 of the Lys residues are covalently attached to a PEG molecule, or the carboxy-terminal amino acid is covalently attached to a PEG molecule;

provided that if $Xaa_{44}$, $Xaa_{45}$, $Xaa_{46}$, or $Xaa_{47}$ is absent each amino acid downstream is absent; and provided that there are 2, 1 or 0 Cys in the molecule;

and provided that if $Xaa_{42}$, $Xaa_{43}$, $Xaa_{44}$, $Xaa_{45}$, $Xaa_{46}$, $Xaa_{47}$, $Xaa_{48}$, or $Xaa_{49}$ is absent each amino acid downstream is absent Preferred embodiments of Formula I-VII include GLP-1 compounds that do not differ from GLP-1(7-37)OH or GLP-1(7-36)$NH_2$ by more than 7 amino acids, by more than 6 amino acids, by more than 5 amino acids, by more than 4 amino acids, or by more than 3 amino acids. It is also preferable that the GLP-1 compounds of Formula I-VII have valine or glycine at position 8 and glutamic acid at position 22. It is also preferable that the GLP-1 compounds of Formula I-VII have valine or glycine at position 8 and glutamic acid at position 30. It is also preferable that the GLP-1 compounds of Formula I-VII have valine or glycine at position 8 and histidine or cysteine at position 37. It is also preferable that the GLP-1 compounds of Formula I-VII have 2 or 1 or 0 cysteine residues. It is also preferable that there is one PEG molecule per GLP-1 compound.

Another embodiment of the invention is a PEGylated GLP-1 compound comprising the amino acid sequence of Formula VIII (SEQ ID NO:10)

```
Formula VIII
                                               (SEQ ID NO: 10)
Xaa7-Xaa8-Xaa9-Xaa10-Xaa11-Xaa12-Xaa13-Xaa14-

Xaa15-Xaa16-Xaa17-Xaa18-Xaa19-Xaa20-Xaa21-Xaa22-

Xaa23-Xaa24-Xaa25-Xaa26-Xaa27-Xaa28-Xaa29-Xaa30-

Xaa31-Xaa32-Xaa33-Xaa34-Xaa35-Xaa36-Xaa37-Xaa38-

Xaa39-Xaa40-Xaa41-Xaa42-Xaa43-Xaa44-Xaa45
``` wherein:

$Xaa_7$ is: L-histidine, D-histidine, desamino-histidine, 2-amino-histidine, β-hydroxy histidine, homohistidine, α-fluoromethyl-histidine, α-methyl-histidine, Arg, Tyr, Ala or Val;

$Xaa_8$ is: Gly, Ser, Ala, or Thr;

$Xaa_9$ is: Glu, Ala or Asp;

$Xaa_{10}$ is: Gly, Ala or Val;

$Xaa_{11}$ is: Thr, Cys or Ala;

$Xaa_{12}$ is: Phe, Cys, Ala, or Tyr;

$Xaa_{13}$ is: Thr or Ser;

$Xaa_{14}$ is: Ser, Ala, or Thr;

$Xaa_{15}$ is: Asp, or Glu;

$Xaa_{16}$ is: Leu, Cys, Ala, Ile, Val, or Met;

$Xaa_{17}$ is: Ser or Ala;

$Xaa_{18}$ is: Lys or Ala;

$Xaa_{19}$ is: Gln or Ala;

$Xaa_{20}$ is: Met, Ala, Leu, Ile, or Val;

$Xaa_{21}$ is: Glu or Ala;

$Xaa_{22}$ is: Glu, Cys, or Ala;

$Xaa_{23}$ is: Glu, Cys, or Ala;

$Xaa_{24}$ is: Ala or Cys;

$Xaa_{25}$ is: Val, Cys, or Ala;

$Xaa_{26}$ is: Arg, Cys, or Ala $Xaa_{27}$ is: Leu, Cys, or Ala;

$Xaa_{28}$ is: Phe, Ala, or Tyr;

$Xaa_{29}$ is: Ile, Val, Leu, Gly, or Met;

$Xaa_{30}$ is: Glu, Cys, Ala, or Asp;

$Xaa_{31}$ is: Trp, Ala, Phe, or Tyr;

$Xaa_{32}$ is: Leu or Ala;

$Xaa_{33}$ is: Lys or Ala;

$Xaa_{34}$ is: Asn, Cys, or Ala;

$Xaa_{35}$ is: Gly or Cys;

$Xaa_{36}$ is: Gly or Cys;

$Xaa_{37}$ is: Pro or Cys $Xaa_{38}$ is: Ser, Cys, NH2, or absent;

$Xaa_{39}$ is: Ser, Cys, NH2, or absent;

$Xaa_{40}$ is: Gly, Cys, NH2 or absent;

Xaa$_{41}$ is: Ala, Cys, NH2 or absent;

Xaa$_{42}$ is: Pro, Cys, NH2 or absent;

Xaa$_{43}$ is Pro, Cys, NH2 or absent;

Xaa$_{44}$ is Pro, Cys, NH2 or absent; and

Xaa$_{45}$ is Ser, Cys, NH2 or absent;

and wherein:

2 or 1 of the Cys residues are covalently attached to a PEG molecule; and provided that there are 2 or 1 Cys in the molecule; further provided that no more than three of Xaa$_9$, Xaa$_{10}$, Xaa$_{11}$, Xaa$_{12}$, Xaa$_{14}$, Xaa$_{15}$, Xaa$_{16}$, Xaa$_{17}$, Xaa$_{18}$, Xaa$_{19}$, Xaa$_{20}$, Xaa$_{21}$, Xaa$_{22}$, Xaa$_{23}$, Xaa$_{24}$, Xaa$_{26}$, Xaa$_{27}$, Xaa$_{30}$, Xaa$_{31}$, Xaa$_{32}$, are Ala; and provided also that, if Xaa$_1$ is His, Arg or Tyr, then at least one of Xaa$_9$, Xaa$_{10}$ and Xaa$_{16}$ is Ala; and, further provided that if Xaa$_{38}$, Xaa$_{39}$, Xaa$_{40}$, Xaa$_{41}$, Xaa$_{42}$, Xaa$_{43}$ or Xaa$_{44}$ is absent each amino acid downstream is absent. Positions 7, 28, 29, 31 and 32 of Formula VIII cannot accommodate a cysteine amino acid without resultant unacceptable loss of activity.

The polyethylene glycol polymers used in the invention ("PEG") preferably have molecular weights between 500 and 100,000 daltons, more preferably between 20,000 and 60,000 daltons, most preferably between 20,000 and 40,000 daltons, may be linear or branched molecules, and may be polyethylene glycol derivatives as described in the art.

The present invention encompasses a method of stimulating the GLP-1 receptor in a subject in need of such stimulation, said method comprising the step of administering to the subject an effective amount of a PEGylated GLP-1 compound described herein. The present invention also encompasses a method of stimulating the GLP-1 receptor in a subject in need of such stimulation, said method comprising the step of administering to the subject an effective amount of an unPEGylated GLP-1 compound with a sequence as shown in SEQ ID NOs 3-10 provided that there are 2 or 1 Cys in the molecule. Subjects in need of GLP-1 receptor stimulation include those with non-insulin dependent diabetes, stress-induced hyperglycemia, obesity, gastric and/or intestinal motility or emptying disorders including, for example, irritable bowel syndrome and functional dyspepsia.

DETAILED DESCRIPTION OF THE INVENTION

Glucagon-Like Peptide 1 (GLP-1) is a 37 amino acid peptide secreted by the L-cells of the intestine in response to food ingestion. Numerous GLP-1 analogs and derivatives have been described in the art. The present invention describes modifications to GLP-1 compounds that result in extended elimination half-life and/or reduced clearance. Incorporation of 1 or 2 Cys residues into particular amino acid sites of the peptide provides a thiol group to which a polyethylene glycol (PEG) or PEG derivative may be covalently attached resulting in a PEGylated GLP-1 compound. Additionally, the lysine residues or the carboxy-terminus of the GLP-1 peptides, analogs or fragments of the invention may be covalently attached to one or more molecules of PEG or a PEG derivative resulting in a molecule with extended elimination half-life and/or reduced clearance.

```
GLP-1 (7-37)OH has the amino acid sequence
of SEQ ID NO: 1:
                                        (SEQ ID NO: 1)
```

```
                              -continued
 7   8   9  10  11  12  13  14  15  16  17
His-Ala-Glu-Gly-Thr-Phe-Thr-Ser-Asp-Val-Ser- 18  19  20  21  22  23  24  25  26  27  28
Ser-Tyr-Leu-Glu-Gly-Gln-Ala-Ala-Lys-Gly-Phe- 29  30  31  32  33  34  35  36  37
Ile-Ala-Trp-Leu-Val-Lys-Gly-Arg-Gly
```

The term "polypeptide" or "peptide" as used herein, is intended to indicate any structural form (e.g., primary, secondary or tertiary form) of an amino acid sequence comprising more than 5 amino acid residues, which may or may not be further modified (e.g., acetylated, carboxylated, phosphorylated, lipidated, or acylated). The term "native" refers to a polypeptide that has an amino acid sequence that is identical to one found in nature. The term "native" is intended to encompass allelic variants of the polypeptide in question.

The term "amino acid" is used herein in its broadest sense, and includes naturally occurring amino acids as well as non-naturally occurring amino acids, including amino acid variants and derivatives. One skilled in the art will recognize, in view of this broad definition, that reference herein to an amino acid includes, for example, naturally occurring proteogenic L-amino acids; D-amino acids; chemically modified amino acids such as amino acid variants and derivatives; naturally occurring non-proteogenic amino acids such as norleucine, β-alanine, ornithine, etc.; and chemically synthesized compounds having properties known in the art to be characteristic of amino acids. Examples of non-naturally occurring amino acids include α-methyl amino acids (e.g., α-methyl alanine), D-amino acids, histidine-like amino acids (e.g., 2-amino-histidine, β-hydroxy-histidine, homohistidine, α-fluoromethyl-histidine and α-methyl-histidine), amino acids having an extra methylene in the side chain ("homo" amino acids) and amino acids in which a carboxylic acid functional group in the side chain is replaced with a sulfonic acid group (e.g., cysteic acid). Preferably, however, the GLP-1 compounds of the present invention comprise only naturally occurring amino acids except as otherwise specifically provided herein.

The term "GLP-1 compound" as used herein, includes native GLP-1, [GLP-1(7-37)OH or GLP-1(7-36)NH$_2$], GLP-1 analogs, GLP-1 derivatives, GLP-1 biologically active fragments, extended GLP-1 or an analog or fragment of an extended GLP-1 peptide (see, e.g., U.S. patent application Ser. Nos. 60/346,474 and 60/405,097), exendin-4 analogs and exendin-4 derivatives comprising one or two Cys residues at particular positions of the peptide as described herein.

By custom in the art, the amino terminus of native GLP-1 (7-37)OH has been assigned residue number 7 and the carboxy-terminus, number 37. The other amino acids in the polypeptide are numbered consecutively, as shown in SEQ ID NO: 1. For example, position 12 is phenylalanine and position 22 is glycine in the native molecule.

A "GLP-1 fragment," or "fragment of a GLP-1 compound" as used herein, is a biologically active polypeptide obtained after truncation of one or more amino acids from the N-terminus and/or C-terminus of a GLP-1 compound. The nomenclature used to describe GLP-1(7-37)OH applies to GLP-1 fragments. For example, GLP-1(9-36)OH denotes a GLP-1 fragment obtained by truncating two amino acids from the N-terminus and one amino acid from the C-terminus. The amino acids in the fragment are denoted by the same number as the corresponding amino acid in GLP-1(7-37)OH. For example, the N-terminal glutamic acid in GLP-1(9-36)OH is at position 9; position 12 is occupied by phenylalanine; and position 22 is occupied by glycine, as in GLP-1(7-37)OH.

GLP-1 compounds include GLP-1 analogs and exendin-4 analogs. To be clear, "exendin-4 analogs" as included within "GLP-1 compounds" always have one or two Cys residues. Preferably, a GLP-1 analog has the amino acid sequence of GLP-1(7-37)OH or an extended GLP-1 peptide as described in U.S. patent application Ser. No. 60/346,474 filed Aug. 1, 2002, or U.S. patent application Ser. No. 60/405,097 filed Aug. 21, 2002, both entitled "Extended Glucagon-Like Peptide-1 Analogs." or a fragment thereof, modified so that 1, 2, 3, 4, 5 or 6 amino acids differ from the amino acid in the corresponding position of GLP-1(7-37)OH or a fragment of GLP-1(7-37)OH or modified so that 0, 1, 2, 3, 4, 5 or 6 amino acids differ from the amino acid in the corresponding position of an extended GLP-1 peptide. Most preferred GLP-1 analogs are described herein in Formulas, I, II, III, IV, V, VI and VII. Most preferred exendin-4 analogs are described herein in Formula VIII.

The term "PEGylated" when referring to a GLP-1 compound of the present invention refers to a GLP-1 compound that is chemically modified by covalent attachment of one or more molecules of polyethylene glycol or a derivative thereof. Furthermore, it is intended that the term "PEG" refers to polyethylene glycol or a derivative thereof as are known in the art (see, e.g., U.S. Pat. Nos. 5,445,090; 5,900,461; 5,932,462; 6,436,386; 6,448,369; 6,437,025; 6,448,369; 6,495,659; 6,515,100 and 6,514,491). Preferably, in PEGylated GLP-1 compounds of the present invention, PEG (or a derivative thereof) is covalently attached to one or more lysine or cysteine residues of the GLP-1 compound. Most preferably, PEG is covalently attached to one or more cysteine residues of the GLP-1 compound. For PEGylated exendin-4 analogs of the present invention, PEG is attached to one or two cysteine residues introduced into exendin-4 or an exendin-4 analog at positions identified in Formula VIII. Optionally, the PEG molecules may be attached to the GLP-1 compound via a linker or spacer molecule (see exemplary spacer molecules described in U.S. Pat. No. 6,268,343).

In the nomenclature used herein to designate GLP-1 compounds, the substituting amino acid and its position is indicated followed by the name of the parent peptide. For example, $Glu_{22}$-GLP-1(7-37)OH designates a GLP-1 compound in which the glycine normally found at position 22 of GLP-1(7-37)OH has been replaced with glutamic acid; $Val_8Glu_{22}$-GLP-1(7-37)OH (or $V_8E_{22}$-GLP-1(7-37)OH) designates a GLP-1 compound in which alanine normally found at position 8 and glycine normally found at position 22 of GLP-1(7-37)OH have been replaced with valine and glutamic acid, respectively. $Val_8$-exendin4 designates a GLP-1 compound in which serine normally found at position 8 of exendin4 has been replaced with a valine. Preferably the GLP-1 compounds of the invention have insulinotropic activity.

"Insulinotropic activity" refers to the ability to stimulate insulin secretion in response to elevated glucose levels, thereby causing glucose uptake by cells and decreased plasma glucose levels. Insulinotropic activity can be assessed by methods known in the art, including using in vivo experiments and in vitro assays that measure GLP-1 receptor binding activity or receptor activation, e.g., assays employing pancreatic islet cells or insulinoma cells, as described in EP 619,322 to Gelfand, et al., and U.S. Pat. No. 5,120,712, respectively. Insulinotropic activity is routinely measured in humans by measuring insulin levels or C-peptide levels.

For the purposes of the present invention an in vitro GLP-1 receptor signaling assay is used to determine whether a PEGylated GLP-1 compound of the present invention will exhibit insulinotropic activity in vivo. Insulinotropic activity is an activity that may be used to demonstrate that the PEGylated GLP-1 compound is biologically active.

"In vitro potency" as used herein, is the measure of the ability of a peptide to activate the GLP-1 receptor in a cell-based assay. In vitro potency is expressed as the "$EC_{50}$" which is the effective concentration of compound that results in 50% activity in a single dose-response experiment. For the purposes of the present invention, in vitro potency is determined using a fluorescence assay that employs HEK-293 cells that stably express the human GLP-1 receptor. These HEK-293 cells have stably integrated a DNA vector having a cAMP response element (CRE) driving expression of the β-lactamase (BLAM) gene. The interaction of a GLP-1 compound (or agonist) with the receptor initiates a signal that results in activation of the cAMP response element and subsequent expression of β-lactamase. The β-lactamase CCF2/AM substrate that emits fluorescence when it is cleaved by β-lactamase (PanVera LLC) can then be added to cells that have been exposed to a specific amount of GLP-1 agonist to provide a measure of GLP-1 agonist potency. The assay is further described in Zlokarnik et al. (1998) Science 279:84-88. The $EC_{50}$ values for the compounds listed in Example 4 were determined using the BLAM assay described above. Relative in vitro potency values may be established by running $Val_8$-GLP-1(7-37)OH or native GLP-1 as a control and assigning the control a reference value of 100%.

The term "plasma half-life" refers to the time in which half of the relevant molecules circulate in the plasma prior to being cleared. An alternatively used term is "elimination half-life." The term "extended" or "longer" used in the context of plasma half-life or elimination half-life indicates there is a statistically significant increase in the half-life of a PEGylated GLP-1 compound relative to that of the reference molecule (e.g., the non-PEGylated form of the peptide or the native peptide) as determined under comparable conditions. Preferably a PEGylated GLP-1 compound of the present invention has an elimination half-life of at least one hour, more preferably at least 3, 5, 7, 10, 15, 20 hours and most preferably at least 24 hours. The half-life reported herein in Example 5 is the elimination half-life; it is that which corresponds to the terminal log-linear rate of elimination. Those of skill in the art appreciate that half-life is a derived parameter that changes as a function of both clearance and volume of distribution.

Clearance is the measure of the body's ability to eliminate a drug. As clearance decreases due, for example, to modifications to a drug, half-life would be expected to increase. However, this reciprocal relationship is exact only when there is no change in the volume of distribution. A useful approximate relationship between the terminal log-linear half-life ($t_{1/2}$). Clearance (C), and volume of distribution (V) is given by the equation: $t_{1/2} \approx 0.693$ (V/C). Clearance does not indicate how much drug is being removed but, rather, the volume of biological fluid such as blood or plasma that would have to be completely freed of drug to account for the elimination. Clearance is expressed as a volume per unit of time. The PEGylated GLP-1 compounds of the present invention preferably have a clearance value of 200 ml/h/kg or less, more preferably 180, 150, 120, 100, 80, 60 ml/h/kg or less and most preferably 50, 40 or 20 ml/h/kg or less (See Example 5).

In the present invention, a Cys amino acid may not be incorporated at positions 7, 28, 29, 31 or 32 or GLP-1 or GLP-1 analog peptides because of loss of activity of the resulting peptide. It is contemplated that all other residues may be replace with a cysteine but it is preferably that such cysteine be incorporated at position(s) selected from the group consisting of 11, 12, 16, 22, 23, 24, 25, 26, 27, 30, 34, 35, 36 and 37 of GLP-1 or GLP-1 analog peptides, with preferably no more than 2 or 1 Cys amino acids per molecule. When Cys amino acids exist in the GLP-1 molecule, it is even more preferred preferred that they are located at position(s) selected from the group consisting of 22, 26, 34, 35, 36 and 37 and even more preferred to exist at position 26 and/or 34. The resulting molecule may be PEGylated at the Cys amino acids resulting in a modified molecule that retains all or a portion of a biological activity while having a longer half-life than that of the unmodified molecule or than that of a native molecule. Alternatively, in the invention, GLP-1 or GLP-1 analog peptides may be PEGylated at one, two or three of the lysine residues at positions 18, 22 and 26; or at the amino acid at the carboxy terminus of the peptide.

Another embodiment of the invention is the unPEGylated GLP-1 compounds with the sequence as shown in SEQ ID NOs 3-10 provided that there are 2 or 1 Cys in the molecule. Applicants discovered that residues at specific position of the GLP-1 compounds can be substituted with Cys and still retain biological activity. These unPEGylated GLP-1 compounds may be intermediates used in the process of producing the PEGylated GLP-1 compounds of the present invention. These compounds may also be used as therapeutics for disorders where an extended half-life is not required, e.g., irritable bowel syndrome.

Once a peptide for use in the invention is prepared and purified, it is modified by covalently linking at least one PEG molecule to Cys or Lys residues or to the carboxy-terminal amino acid. It is difficult to endow delicate peptide or protein molecules with suitable new properties by attaching polymers without causing loss of their functionality. A wide variety of methods have been described in the art to produce covalently conjugated to PEG and the specific method used for the present invention is not intended to be limiting (for review article see, Roberts, M. et al. *Advanced Drug Delivery Reviews,* 54:459-476, 2002). Carboxy-terminal attachment of PEG may be attached via enzymatic coupling using recombinant GLP-1 peptide as a precursor or alternative methods known in the art and described, for example, in U.S. Pat. No. 4,343,898 or *International Journal of Peptide & Protein Research.* 43:127-38, 1994. PEGylation of proteins may overcome many of the pharmacological and toxicological/immunological problems associated with using peptides or proteins as therapeutics. However, for any individual peptide it is uncertain whether the PEGylated form of the peptide will have significant loss in bioactivity as compared to the unPEGylated form of the peptide.

The bioactivity of PEGylated proteins can be effected by factors such as: i) the size of the PEG molecule; ii) the particular sites of attachment; iii) the degree of modification; iv) adverse coupling conditions; v) whether a linker is used for attachment or whether the polymer is directly attached; vi) generation of harmful co-products; vii) damage inflicted by the activated polymer; or viii) retention of charge. Depending on the coupling reaction used, polymer modification of cytokines, in particular, has resulted in dramatic reductions in bioactivity. [Francis, G. E., et al., (1998) PEGylation of cytokines and other therapeutic proteins and peptides: the importance of biological optimization of coupling techniques, *Intl. J. Hem.* 68:1-18].

PEGylated GLP-1 compounds of the present invention have an in vitro biological activity that is at least 0.5% that of native GLP-1 or more preferably that of Val$^8$-GLP-1(7-37) OH. More preferably, the PEGylated GLP-1 compound of the present invention has an in vitro biological activity that is at least 1% or 3% that of native GLP-1 or more preferably that of Val$_8$-GLP-1(7-37)OH. Such biological activity may be determined by the in vitro potency assay as described herein (Example 4) or by other GLP-1 assays known in the art. Although some PEGylated GLP-1 compounds of the invention may have biological activity lower than that of native GLP-1 or of Val$_8$-GLP-1(7-37)OH as measured in a particular assay; this activity decrease is compensated by the compound's extended half-life and/or lower clearance value and may even be a favorable characteristic for a GLP-1 compound with an extended elimination half-life.

It is further contemplated that the positions of the GLP-1 peptide which have been found to accommodate a cysteine residue without elimination of biological activity may be substituted with a cysteine in the analogous position of exendin-4 and result in an exendin-4 analog still capable of binding the GLP-1 receptor. Preferably there are no more than 2 or 1 Cys amino acids per exendin-4 analog of the invention. Preferably Cys that exist in the molecule are at positions selected from the group consisting of 11, 12, 16, 22, 23, 24, 25, 26, 27, 30, 34, 35, 36, 37, 38, 39, 40, 41, 42, 43 and 44 (see Formula VIII); preferably positions selected from the group consisting of 22, 26, 34, 35, 36, 37, 38, 39, 40, 41, 42, 43 and 44; even more preferably positions 26 and/or 34. Cys amino acids present in the molecule are covalently attached to a PEG molecule resulting in a PEGylated exendin-4 analog with an elimination half-life longer than that of native exendin-4. Preferably a PEGylated exendin-4 analog peptide (as described in Formula VIII) of the present invention has a biological activity that is at least 0.5%, 1.0%, 3%, 10%, 30%, or 50% that of the unPEGylated exendin-4 analog. The sequence of wild type exendin 4 is: HGEGTFTSDL-SKQMEEEAVRLFIEWLKNGGPSSGAPPS (SEQ ID NO: 11).

In its typical form, PEG is a linear polymer with terminal hydroxyl groups and has the formula HO—CH$_2$CH$_2$—(CH$_2$CH$_2$O)n-CH$_2$CH$_2$—OH, where n is from about 8 to about 4000. The terminal hydrogen may be substituted with a protective group such as an alkyl or alkanol group. Preferably, PEG has at least one hydroxy group, more preferably it is a terminal hydroxy group. It is this hydroxy group which is preferably activated to react with the peptide. There are many forms of PEG useful for the present invention. Numerous derivatives of PEG exist in the art and are suitable for use in the invention. (See, e.g., U.S. Pat. Nos. 5,445,090; 5,900,461; 5,932,462; 6,436,386; 6,448,369; 6,437,025; 6,448,369; 6,495,659; 6,515,100 and 6,514,491 and Zalipsky, S. *Bioconjugate Chem.* 6:150-165, 1995). The PEG molecule covalently attached to GLP-1 compounds in the present invention is not intended to be limited to a particular type. PEG's molecular weight is preferably from 500-100,000 daltons and more preferably from 20,000-60,000 daltons and most preferably from 20,000-40,000 daltons. PEG may be linear or branched and PEGylated GLP-1 compounds of the invention may have 1, 2, 3, 4, 5 or 6 PEG molecules attached to the peptide. It is most preferably that there be one PEG molecule per PEGylated GLP-1 compound molecule; however, when there are more than PEG molecules per peptide molecule, it is preferred that there be no more than six. It is further contemplated that both ends of the PEG molecule may be homo- or heroly-functionalized for crosslinking two or more GLP-1 compounds together.

The present invention provides GLP-1 compounds with one or more PEG molecules covalently attached thereto. One method for preparing the PEGylated GLP-1 compounds of the present invention involves the use of PEG-maleimide to directly attach PEG to a thiol group of the peptide. The introduction of a thiol functionality can be achieved by adding or inserting a Cys residue onto or into the peptide at positions described above. A thiol functionality can also be introduced onto the side-chain of the peptide (e.g. acylation of lysine ε-amino group of a thiol-containing acid). A PEGylation process of the present invention utilizes Michael addition to form a stable thioether linker. The reaction is highly specific and takes place under mild conditions in the presence of other functional groups. PEG maleimide has been used as a reactive polymer for preparing well-defined, bioactive PEG-protein conjugates. It is preferable that the procedure uses a molar excess of a thiol-containing GLP-1 compound relative to PEG maleimide to drive the reaction to completion. The reactions are preferably performed between pH 4.0 and 9.0 at room temperature for 15 to 40 hours. The excess of unPEGylated thiol-containing peptide is readily separated from the PEGylated product by conventional separation methods. Exemplary conditions required for PEGylation of GLP-1 compounds are set forth in Example 1. Cysteine PEGylation may be performed using PEG maleimide or bifurcated PEG maleimide.

GLP-1 compounds have a variety of biological activities. For example, GLP-1 has been found to stimulate insulin release, thereby causing glucose uptake by cells and decreased serum glucose levels [see, e.g., Mojsov, S., (1992) *Int. J. Peptide Protein Research,* 40:333]. GLP-1 is particularly promising as a treatment for non-insulin dependent diabetes mellitus (NIDDM) as it does present a risk of hypoglycemia as do present NIDDM treatments. GLP-1 is also contemplated to be a treatment for obesity, irritable bowel syndrome and functional dyspepsia.

It is contemplated that a use of a PEGylated GLP-1 compound of the present invention includes use in the manufacture of a medicament for the treatment of non-insulin dependent diabetes, obesity, stroke, myocardial infarction, irritable bowel syndrome or functional dyspepsia. PEGylation of a GLP-1 compound may be combined with other modifications known in the art to increase GLP-1 half-life (see, e.g, U.S. patent application Ser. No. 60/346,474 filed Aug. 1, 2002, and U.S. patent application Ser. No. 60/405,097 filed Aug. 21, 2002) and thereby increase the half-life of the compound even further than PEGylation alone or the other modification method alone.

As used herein, the term "GLP-1 compound" also includes pharmaceutically acceptable salts of the compounds described herein. A GLP-1 compound of this invention can possess a sufficiently acidic, a sufficiently basic, or both functional groups, and accordingly react with any of a number of inorganic bases, and inorganic and organic acids, to form a salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

The PEGylated GLP-1 compounds of the present invention are particularly suited for parenteral administration, they can be also be delivered orally, by nasal administration, or by inhalation. Parenteral administration can include, for example, systemic administration, such as by intramuscular, intravenous, subcutaneous, or intraperitoneal injection. The PEGylated GLP-1 compounds can be administered to the subject in conjunction with an acceptable pharmaceutical carrier, diluent or excipient as part of a pharmaceutical composition for treating the diseases discussed above. The pharmaceutical composition can be a solution or, if administered parenterally, a suspension of the GLP-1 compound or a suspension of the GLP-1 compound complexed with a divalent metal cation such as zinc. Suitable pharmaceutical carriers may contain inert ingredients which do not interact with the peptide or peptide derivative. Standard pharmaceutical formulation techniques may be employed such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringers-lactate and the like. Some examples of suitable excipients include lactose, dextrose, sucrose, trehalose, sorbitol, and mannitol.

The PEGylated GLP-1 compounds of the invention may be formulated for administration such that blood plasma levels are maintained in the efficacious range for extended time periods. The main barrier to effective oral peptide drug delivery is poor bioavailability due to degradation of peptides by acids and enzymes, poor absorption through epithelial membranes, and transition of peptides to an insoluble form after exposure to the acidic pH environment in the digestive tract. Oral delivery systems for peptides such as those encompassed by the present invention are known in the art. For example, PEGylated GLP-1 compounds can be encapsulated using microspheres and then delivered orally. For example, PEGylated GLP-1 compounds can be encapsulated into microspheres composed of a commercially available, biocompatible, biodegradable polymer, poly(lactide-co-glycolide)-COOH and olive oil as a filler. See Joseph, et al. (2000) Diabetologia 43:1319-1328. Other types of microsphere technology is also available commercially such as Medisorb® and Prolease® biodegradable polymers from Alkermes. Medisorb® polymers can be produced with any of the lactide isomers. Lactide:glycolide ratios can be varied between 0:100 and 100:0 allowing for a broad range of polymer properties. This allows for the design of delivery systems and implantable devices with resorption times ranging from weeks to months. Emisphere has also published numerous articles discussing oral delivery technology for peptides and proteins. For example, see WO 9528838 by Leone-bay et al. which discloses specific carriers comprised of modified amino acids to facilitate absorption.

The PEGylated GLP-1 compounds described herein can be used to treat subjects with a wide variety of diseases and conditions. PEGylated GLP-1 compounds encompassed by the present invention exert their biological effects by acting at a receptor referred to as the "GLP-1 receptor" (see Dillon et al. (1993) Cloning and Functional Expression of the Human Glucagon-like Peptide-1 (GLP-1) Receptor, *Endocrinology,*

133:1907-1910). Subjects with diseases and/or conditions that respond favorably to GLP-1 receptor stimulation or to the administration of GLP-1 compounds can therefore be treated with the PEGylated GLP-1 compounds of the present invention. These subjects are said to "be in need of treatment with GLP-1 compounds" or "in need of GLP-1 receptor stimulation".

Included are subjects with non-insulin dependent diabetes, insulin dependent diabetes, stroke (see WO 00/16797 by Efendic), myocardial infarction (see WO 98/08531 by Efendic), obesity (see WO 98/19698 by Efendic), catabolic changes after surgery (see U.S. Pat. No. 6,006,753 to Efendic), functional dyspepsia and irritable bowel syndrome (see WO 99/64060 by Efendic). Also included are subjects requiring prophylactic treatment with a GLP-1 compound, e.g., subjects at risk for developing non-insulin dependent diabetes (see WO 00/07617). Additional subjects include those with impaired glucose tolerance or impaired fasting glucose, subjects whose body weight is about 25% above normal body weight for the subject's height and body build, subjects with a partial pancreatectomy, subjects having one or more parents with non-insulin dependent diabetes, subjects who have had gestational diabetes and subjects who have had acute or chronic pancreatitis are at risk for developing non-insulin dependent diabetes.

The PEGylated GLP-1 compounds of the present invention can be used to normalize blood glucose levels, prevent pancreatic β-cell deterioration, induce β-cell proliferation, stimulate insulin gene transcription, up-regulate IDX-1/PDX-1 or other growth factors, improve β-cell function, activate dormant β-cells, differentiate cells into β-cells, stimulate β-cell replication, inhibit β-cell apoptosis, regulate body weight and induce weight loss.

An "effective amount" of a PEGylated GLP-1 compound is the quantity that results in a desired therapeutic and/or prophylactic effect without causing unacceptable side-effects when administered to a subject in need of GLP-1 receptor stimulation. A "desired therapeutic effect" includes one or more of the following: 1) an amelioration of the symptom(s) associated with the disease or condition; 2) a delay in the onset of symptoms associated with the disease or condition; 3) increased longevity compared with the absence of the treatment; and 4) greater quality of life compared with the absence of the treatment. For example, an "effective amount" of a PEGylated GLP-1 compound for the treatment of diabetes is the quantity that would result in greater control of blood glucose concentration than in the absence of treatment, thereby resulting in a delay in the onset of diabetic complications such as retinopathy, neuropathy or kidney disease. An "effective amount" of a PEGylated GLP-1 compound for the prevention of diabetes is the quantity that would delay, compared with the absence of treatment, the onset of elevated blood glucose levels that require treatment with anti-hypoglycaemic drugs such as sulfonyl ureas, thiazolidinediones, insulin and/or bisguanidines.

An "effective amount" of the PEGylated GLP-1 compound administered to a subject will also depend on the type and severity of the disease and on the characteristics of the subject, such as general health, age, sex, body weight and tolerance to drugs. Typically, the PEGylated GLP-1 compounds of the present invention will be administered such that plasma levels are within the range of about 5 picomoles/liter and about 200 picomoles/liter. Optimum plasma levels for $Val_8$-GLP-1(7-37)OH were determined to be between 30 picomoles/liter and about 200 picomoles/liter.

A typical dose range for the PEGylated GLP-1 compounds of the present invention will range from about 0.01 mg per day to about 1000 mg per day for an adult. Preferably, the dosage ranges from about 0.1 mg per day to about 100 mg per day, more preferably from about 1.0 mg/day to about 10 mg/day.

A "subject" is a mammal, preferably a human, but can also be an animal, e.g., companion animals (e.g., dogs, cats, and the like), farm animals (e.g., cows, sheep, pigs, horses, and the like) and laboratory animals (e.g., rats, mice, guinea pigs, and the like).

The peptides used to generate the PEGylated GLP-1 compounds of the present invention can be prepared by using standard methods of solution phase or solid-phase peptide synthesis techniques. Peptide synthesizers are commercially available from, for example, Applied Biosystems in Foster City Calif. Reagents for solid phase synthesis are commercially available, for example, from Midwest Biotech (Fishers, Ind.). Solid phase peptide synthesizers can be used according to manufacturers instructions for blocking interfering groups, protecting the amino acid to be reacted, coupling, decoupling, and capping of unreacted amino acids.

Typically, an α-N-carbamoyl protected amino acid and the N-terminal amino acid on the growing peptide chain on a resin is coupled at room temperature in an inert solvent such as dimethylformamide, N-methylpyrrolidone or methylene chloride in the presence of coupling agents such as dicyclohexylcarbodiimide and 1-hydroxybenzotriazole and a base such as diisopropylethylamine. The α-N-carbamoyl protecting group is removed from the resulting peptide resin using a reagent such as trifluoroacetic acid or piperidine, and the coupling reaction repeated with the next desired N-protected amino acid to be added to the peptide chain. Suitable amine protecting groups are well known in the art and are described, for example, in Green and Wuts, "*Protecting Groups in Organic Synthesis*", John Wiley and Sons, 1991, the entire teachings of which are incorporated by reference. Examples include t-butyloxycarbonyl (tBoc) and fluorenylmethoxycarbonyl (Fmoc).

The peptides are also synthesized using standard automated solid-phase synthesis protocols using t-butoxycarbonyl- or fluorenylmethoxycarbonyl-alpha-amino acids with appropriate side-chain protection. After completion of synthesis, peptides are cleaved from the solid-phase support with simultaneous side-chain deprotection using standard hydrogen fluoride methods. Crude peptides are then further purified using Reversed-Phase Chromatography on Vydac C18 columns using acetonitrile gradients in 0.1% trifluoroacetic acid (TFA). To remove acetonitrile, peptides are lyophilized from a solution containing 0.1% TFA, acetonitrile and water. Purity can be verified by analytical reversed phase chromatography. Identity of peptides can be verified by mass spectrometry. Peptides can be solubilized in aqueous buffers at neutral pH.

The invention is illustrated by the following examples that are not intended to be limiting in any way.

EXAMPLES

Example 1

PEGylation of GLP-1 Related Analogs

PEGylation reactions are run under conditions that permit the formation of a thioether bond. Specifically, the pH of the solution ranges from about 4 to 9 and the thiol-containing peptide concentrations range from 1 to 10 molar excess of methoxy-PEG2-MAL concentration. The PEGylation reactions are normally run at room temperature. The PEGylated GLP-1 peptide is then isolated using reverse-phase HPLC or size exclusion chromatography (SEC). PEGylated GLP-1 analogues are characterized using analytical RP-HPLC, HPLC-SEC, SDS-PAGE, and/or MALDI Mass Spectrometry.

Thiol-containing GLP-1 peptides are reacted with 40 kDa polyethylene glycol-maleimide (PEG-maleimide) to produce derivatives with PEG covalently attached via a thioether bond. For example, peptide Cex-51-C ($V_8E_{22}I_{33}C_{45}$ GLP-1, 45aa in length; 7.5 mg, 1.8 μmol) is dissolved in 2 ml of 200 mM phosphate buffer containing 20 mM EDTA, pH 7.4. The solution is then purged with argon. To this solution is added 40 mg of methoxy-PEG2-MAL, a bifurcated PEG maleimide (Lot# PT-02B-10, Shearwater Polymers, Inc., Huntsville, Ala.) (0.55:1 mole/mole ratio of PEG to peptide). The reaction is performed for 2 hours. Then 25 mg of the PEGylated peptide is purified by RP-HPLC, characterized by size-exclusion HPLC, and tested for in vitro activity.

Example 2

40 kDa-PEG-maleimide Reaction with GLP Analogs

GLP-1 analogs such as $C_{16}E_{22}V_8$GLP and $V_8C_{38}$ GLP are selectively PEGylated at the introduced cysteine residue using maleimide-activated bifurcated 40 kDa mPEG (Shearwater Polymers, Inc.). For the PEGylation reaction, the peptide to be PEGylated is dissolved in 100 mM TRIS buffer at pH 8.0 and a 1.25-fold molar excess of bulk 40 kDa-mPEG is added. The reaction is allowed to stir at room temperature for 2-3 hours and then dialyzed overnight (7 kDa membrane) against 10 mM citrate, 10 mM phosphate, pH 7.4 at approximately 5° C. The PEGylated-GLP molecules are purified by anion exchange chromatography on a Mono-Q column (Amersham Biosciences Corp, Piscataway, N.J.) using a NaCl gradient at neutral pH.

Example 3

DSPE-3.4 kDa-PEG-maleimide Reaction with GLP-1 Analogs

GLP-1 analogs such as $C_{16}E_{22}V_8$GLP-1 and $V_8C_{38}$GLP-1 are selectively PEGylated at the introduced cysteine residue using maleimide-activated 3.4 kDa mPEG terminated with a lipid, distearoyl phosphatidyl ethanolamine (DSPE) (Shearwater Polymers, Inc.). For the PEGylation reaction, the peptide is dissolved in 100 mM TRIS buffer at pH 8 and a 1.25-fold molar excess of bulk DSPE-3.4 kDa-PEG-maleimide is added. Absolute ethanol is added to approximately 17% to assist in solubilizing the DSPE-3.4 kDa-PEG-maleimide. The reaction is allowed to stir at room temperature for 2-3 hours and then dialyzed overnight (7 kDa membrane) against 10 mM citrate, 10 mM phosphate, pH 7.4 at approximately 5° C. The PEGylated-peptide is purified by anion exchange chromatography on a Mono-Q column (Amersham Biosciences Corp, Piscataway, N.J.) using a NaCl gradient at neutral pH.

Example 4

In Vitro Activity Assay

HEK-293 cells expressing the human GLP-1 receptor, using the PanVera LLC CRE-BLAM system, are seeded at 20,000 to 40,000 cells/well/100 μL DMEM medium with 10% FBS into a poly-d-lysine coated 96 well black, clear-bottom plate. The day after seeding, the medium is flicked off and 80 μl plasma-free DMEM medium is added. On the third day after seeding, 20 μl of plasma-free DMEM medium with 0.5% BSA containing different concentrations of PEGylated GLP-1 compound is added to each well to generate a dose response curve. Generally, fourteen dilutions containing from 3 nanomolar to 30 nanomolar PEGylated peptide are used to generate a dose response curve from which $EC_{50}$ values can be determined. After 5 hours of incubation with the PEGylated peptide, 20 μl of β-lactamase substrate (CCF2/AM, PanVera LLC) is added and incubation continued for 1 hour at which time fluorescence is determined on a cytofluor. The assay is further described in Zlokarnik, et al. (1998), Science, 278:84-88. The following PEGylated GLP-1 peptides were tested as described and had $EC_{50}$ values stated below (with $V_8$GLP-1 equal to 100%):

| | |
|---|---|
| $V_8C_{16}$-3.4 kDa DPSE-PEG | 4% |
| $V_8$-3.4 kDa PEG-FMOC | 87% |
| $V_8C_{38}$-3.4 kDa DPSE-PEG | 18% |
| $V_8C_{38}$-40 kDa PEG | 3% |
| $V_8E_{22}C_{16}$-40 kDa PEG | 0.7% |
| $V_8E_{22}I_{33}C_{45}$-40 kDa PEG (CEX-51) | 9.4 +/− 1.5% [n = 5] |

Example 5

Pharmacokinetic Analysis of Derivatized GLP-1 Peptide

A PEGylated GLP-1 analog ($V_8E_{22}I_{33}C_{45}$-40 kDa PEG (PEGylated, $C_{45}$-modified CEX-51)) is administered by intravenous (IV) or subcutaneous (SC) routes at a dose of 0.1 mg/kg to male SD rats. The animals (2 rats per timepoint for IV, 3 rats for timepoint for SC) are bled at various times between 0 and 336 hours after dosing. Plasma is collected from each sample and analyzed by radioimmunoassay. Pharmacokinetic parameters are calculated using model-dependent (IV data) and independent (SC data) methods (WinNonlin Pro). A representation of the pharmacokinetic parameters is reported in the Table 1 below. By IV administration, the PEGylated GLP-1 analog has an elimination half-life of approximately 1.5 days while by SC administration the PEGylated GLP-1 analog has an elimination half-life of approximately 1.3 days. No adverse clinical observations are associated with IV or SC administration of 0.1 mg/kg $V_8E_{22}I_{33}C_{45}$-40 kDa PEG. Prolonged elimination half-life, slow clearance and relatively high subcutaneous bioavailability (approximately 60%) are observed for the compound.

TABLE 1

| Compound | Route | $C_{max}{}^a$ (ng/mL) | $T_{max}{}^b$ (d) | $AUC_{0-\infty}{}^c$ (ng * h/mL) | $t_{1/2}{}^d$ (d) | $CL/F^e$ (mL/h/kg) | $Vss/F^f$ (mL/kg) | $\%\,F^g$ |
|---|---|---|---|---|---|---|---|---|
| $V_8E_{22}I_{33}C_{45}$- | IV | 1135 | 0.003 | 30293 | 1.5 | 3.3 | 161 | |
| 40 kDa PEG | SC | 187 | 1-2 | 18128 | 1.3 | 5.5 | 256 | 60 |

[a] Maximum observed plasma concentration.
[b] Time of maximum observed plasma concentration.
[c] Area under the plasma concentration-time curve measured from 0 to infinity.
[d] Elimination half-life in days.
[e] Total body clearance as a function of bioavailability.
[f] Volume of distribution at steady state as a function of bioavailability.
[g] Percent bioavailability.

When $V_8$-GLP(7-37)OH is similarly IV administered to Fischer 344 rats at a dose of 10 μg/kg, profoundly different clearance and elimination half-life values are obtained as listed below.

Clearance: 1449 ml/hr/kg t½ (hr): 0.05

A PEGylated GLP-1 analog ($V_8E_{22}I_{33}C_{45}$-40 kDa PEG (PEGylated, $C_{45}$-modified CEX-51)) is administered by intravenous (IV) or subcutaneous (SC) routes at a dose of 0.1 mg/kg to male cynomolgus monkeys. The animals are bled at various times between 0 and 336 hours after dosing. Plasma is collected from each sample and analyzed by radioimmunoassay. Pharmacokinetic parameters are calculated using model-dependent (IV data) and independent (SC data) methods (WinNonlin Pro). A representation of the pharmacokinetic parameters is reported in the Table 2 below. By IV administration, the PEGylated GLP-1 analog has an elimination half-life of approximately 59.5 hours while by SC administration the PEGylated GLP-1 analog has an elimination half-life of approximately 61.6 hours.

TABLE 2

| | | | IV | | | | |
|---|---|---|---|---|---|---|---|
| Dose (mg/kg) | Animal # | $C_{max}{}^a$ (ng/mL) | $T_{max}{}^b$ (h) | $AUC_{0-\infty}{}^c$ (ng * h/mL) | $t_{1/2}{}^d$ (h) | CL (mL/h/kg) | Vss (mL/kg) |
| 0.1 | I00473 | 1662 | 1.0 | 149279 | 59.5 | 0.67 | 57.5 |
| | I00474 | 2282 | 4.0 | 130341 | 42.1 | 0.77 | 46.6 |
| | I00477 | 2672 | 0.0 | 215992 | 76.8 | 0.46 | 51.3 |
| | Mean | 2205 | 1.7 | 165204 | 59.5 | 0.63 | 51.8 |
| | SD | 509 | 2.1 | 1244991 | 17.4 | 0.16 | 5.5 |

| | | | SC | | | | |
|---|---|---|---|---|---|---|---|
| Dose (mg/kg) | Animal # | $C_{max}{}^a$ (ng/mL) | $T_{max}{}^b$ (h) | $AUC_{0-\infty}{}^c$ (ng * h/mL) | $t_{1/2}{}^d$ (h) | $CL/F^e$ (mL/h/kg) | $Vss/F^f$ (mL/kg) |
| 0.1 | I00478 | 657 | 72.0 | 113518 | 64.4 | 0.88 | 81.8 |
| | I00480 | 976 | 48.0 | 138306 | 58.8 | 0.72 | 61.3 |
| | Mean | 817 | 60.0 | 125912 | 61.6 | 0.80 | 71.6 |

[a] Maximum observed plasma concentration.
[b] Time of maximum observed plasma concentration.
[c] Area under the plasma concentration-time curve measured from 0 to infinity.
[d] Elimination half-life.
[e] Total body clearance as a function of bioavailability.
[f] Volume of distribution as a function of bioavailability.
SD = Standard deviation.

Example 6

Pharmacodynamic Analysis of Derivatized GLP-1 Peptide

A PEGylated GLP-1 analog ($V_8E_{22}I_{33}C_{45}$-40 kDa PEG (PEGylated, $C_{45}$-modified CEX-51)) is administered by subcutaneous (SC) route at doses of 3 nmol/kg (12.33 mg/kg=0.62 μg (microgram)/50 g mouse) or 10 nmol/kg (41 mg/kg=2 μg (microgram)/50 g mouse) to male C57BL/6OlaHsd-Lep$^{ob}$ mice versus a vehicle only control. The animals (6 mice per timepoint) are dosed with a single injection of either the PEGylated GLP-1 analog or vehicle at 11:00 am. The mice are then fasted overnight and an IPTGG (1 g dextrose/kg i.p.) is performed. Repeat samples for glucose and insulin are taken pre and after the glucose injection at 15, 30, 60, 90, and 120 minutes. A representation of the pharmacodynamic parameters is reported in the Tables below.

| | | glucose AUC | | |
|---|---|---|---|---|
| | | vehicle | 3 nmol PEG | 10 nmol PEG |
| | | 85965.75 | 28206 | 29765.25 |
| | | 58198.5 | 34884 | 22603.5 |
| | | 60381 | 33291 | 48125.25 |
| | | 73320.75 | 55793.25 | 54038.25 |
| | | 71703 | 48422.25 | 25024.5 |
| | | 72067.5 | 46707.75 | 24808.5 |
| | Average | 70272.75 | 41217.38 | 34060.88 |
| | St. Error | 4100.657 | 4346.437 | 5519.325 |
| | pValue | | 0.000659 | 0.000365 |

| Strain | Mouse ID | GRP | Day 0 Weight | Day 0 Glucose | Day 0 Actual Glucose |
|---|---|---|---|---|---|
| | | | Vehicle | | |
| ob/ob | MR | A | 49.7 | 231.4 | 462.8 |
| ob/ob | MS | A | 46.9 | 260.5 | 521 |
| ob/ob | MZ | A | 48.5 | 206.3 | 412.6 |
| ob/ob | NA | A | 47.1 | 209.6 | 419.2 |
| ob/ob | NI | A | 46.8 | 180.3 | 360.6 |
| ob/ob | NK | A | 48.7 | 222 | 444 |
| | | Average | 47.95 | | 436.7 |
| | | St. Error | 0.48563 | | 21.99944 |
| | | 3 nmol GLP-1 PEG | | | |
| ob/ob | MO | C | 49.4 | 187.1 | 374.2 |
| ob/ob | MP | C | 45.7 | 212.8 | 425.6 |
| ob/ob | MT | C | 53.3 | 253.5 | 507 |
| ob/ob | NC | C | 49.9 | 226 | 452 |

-continued

| | | | | | |
|---|---|---|---|---|---|
| ob/ob | NE | C | 50.3 | 247 | 494 |
| ob/ob | NG | C | 49.5 | 207.7 | 415.4 |
| | Average | | 49.6833 | | 444.7 |
| | St. Error | | 0.99144 | | 20.46022 |
| 10 nmol GLP-1 PEG | | | | | |
| ob/ob | MJ | D | 49.3 | 259 | 518 |
| ob/ob | ML | D | 47.4 | 221.9 | 443.8 |

-continued

| | | | | | |
|---|---|---|---|---|---|
| ob/ob | MU | D | 46.4 | 232.6 | 465.2 |
| ob/ob | MY | D | 48.2 | 227.6 | 455.2 |
| ob/ob | NB | D | 51.5 | 185.7 | 371.4 |
| ob/ob | ND | D | 42.6 | 196.5 | 393 |
| | Average | | 47.5667 | | 441.1 |
| | St. Error | | 1.22384 | | 21.50366 |

| Mouse ID | Dose | Time 0 Actual Glucose | Time 15 Actual Glucose | Time 30 Actual Glucose | Time 60 Actual Glucose | Time 90 Actual Glucose | Time 120 Actual Glucose |
|---|---|---|---|---|---|---|---|
| | | | | Vehicle | | | |
| MR | 0.0994 | 124.8 | 566.7 | 771.9 | 869.1 | | 668.4 |
| MS | 0.0938 | 83.4 | 299.1 | 568.8 | 759.3 | | 204 |
| MZ | 0.097 | 130.5 | 468.6 | 597.3 | 609.3 | | 383.4 |
| NA | 0.0942 | 247.2 | 577.2 | 612.3 | 623.4 | 528.9 | 699.3 |
| NI | 0.0936 | 174.6 | 469.2 | 628.2 | 635.4 | 506.1 | 687.6 |
| NK | 0.0974 | 267 | 563.4 | 649.8 | 662.7 | 495 | 572.4 |
| | Ave | 171.25 | 490.7 | 638.15 | 693.2 | 510 | 535.85 |
| | StError | 29.71165596 | 43.2838538 | 28.99511166 | 41.42960294 | 9.978476838 | 82.05989581 |
| | | | | 3 nmol GLP-1 PEG | | | |
| MO | 0.0988 | 70.2 | 206.4 | 325.2 | 240.9 | | 214.2 |
| MP | 0.0914 | 96.6 | 386.7 | 408 | 295.2 | | 196.5 |
| MT | 0.1066 | 84 | 308.7 | 369.6 | 273.3 | | 247.2 |
| NC | 0.0998 | 156 | 481.2 | 521.7 | 532.8 | 449.1 | 389.7 |
| NE | 0.1006 | 158.7 | 453.6 | 531 | 287.1 | 258 | 518.7 |
| NG | 0.099 | 83.7 | 433.5 | 461.4 | 378.6 | 310.5 | 405.3 |
| | Ave | 108.2 | 378.35 | 436.15 | 334.65 | 339.2 | 328.6 |
| | StError | 15.91596683 | 42.33590084 | 33.90384197 | 43.80457168 | 57.00166664 | 52.57307296 |
| | pValue | 0.074622229 | 0.127534361 | 0.012940369 | 0.004544365 | 0.073533898 | 0.021860517 |
| | | | | 10 nmol GLP-1 PEG | | | |
| MJ | 0.0986 | 91.2 | 164.4 | 312.3 | 290.1 | | 217.8 |
| ML | 0.0948 | 68.1 | 318.6 | 285.3 | 152.1 | | 135 |
| MU | 0.0928 | 114.6 | 384.6 | 489.3 | 420.3 | | 385.8 |
| MY | 0.0964 | 186 | 531.6 | 606.3 | 447.3 | 347.1 | 363.3 |
| NB | 0.103 | 92.4 | 354 | 261.6 | 151.5 | 117 | 210.6 |
| ND | 0.0852 | 90.3 | 277.5 | 272.7 | 209.4 | 147.6 | 147 |
| | Ave | 107.1 | 338.45 | 371.25 | 278.45 | 203.9 | 243.25 |
| | StError | 16.88549674 | 49.69268055 | 58.24718448 | 53.42159208 | 72.14284441 | 43.7524685 |
| | pValue | 0.049860093 | 0.06660094 | 0.013403998 | 0.002986998 | 0.040209038 | 0.018193438 |
| | | 0 | 15 | 30 | 60 | 90 | 120 |
| Vehicle | Ave | 171.25 | 490.7 | 638.15 | 693.2 | 510 | 535.85 |
| 3 nmol | Ave | 108.2 | 378.35 | 436.15 | 334.65 | 339.2 | 328.6 |
| 10 nmol | Ave | 107.1 | 338.45 | 371.25 | 278.45 | 203.9 | 243.25 |

| Mouse ID | Dose | Time 0 Actual Insulin | Time 15 Actual Insulin | Time 30 Actual Insulin | Time 60 Actual Insulin | Time 90 Actual Insulin | Time 120 Actual Insulin |
|---|---|---|---|---|---|---|---|
| | | | | Vehicle | | | |
| MR | 0.0994 | 2.7 | 2.7 | 2.7 | 2.7 | | 3.3 |
| MS | 0.0938 | 12.3 | 3.6 | 2.7 | 2.7 | | 6.9 |
| MZ | 0.097 | 2.7 | 2.7 | 2.7 | 2.7 | | 5.1 |
| NA | 0.0942 | 6.3 | 2.7 | 2.7 | 2.7 | 3.3 | 3.6 |
| NI | 0.0936 | 3.3 | 2.7 | 2.7 | 2.7 | 2.7 | 3.3 |
| NK | 0.0974 | 5.4 | 2.7 | 2.7 | 2.7 | 3 | 4.2 |
| | Ave | 5.45 | 2.85 | 2.7 | 2.7 | 3 | 4.4 |
| | StError | 1.498832879 | 0.15 | 0 | 0 | 0.173205081 | 0.572712843 |
| | | | | 3 nmol GLP-1 PEG | | | |
| MO | 0.0988 | 4.8 | 3.6 | 5.7 | 4.8 | | 2.7 |
| MP | 0.0914 | 5.7 | 16.5 | 12.6 | 8.7 | | 9.6 |
| MT | 0.1066 | 5.4 | 4.5 | 4.8 | 8.4 | | 2.7 |

-continued

| Mouse ID | Dose | Time 0 Actual Insulin | Time 15 Actual Insulin | Time 30 Actual Insulin | Time 60 Actual Insulin | Time 90 Actual Insulin | Time 120 Actual Insulin |
|---|---|---|---|---|---|---|---|
| NC | 0.0998 | 70.8 | 59.4 | 69.9 | 24.6 | 32.7 | 30 |
| NE | 0.1006 | 27.9 | 14.7 | 24.6 | 11.4 | 12.9 | 25.2 |
| NG | 0.099 | 12.6 | 13.8 | 10.8 | 12 | 12.6 | 19.5 |
| | ave | 21.2 | 18.75 | 21.4 | 11.65 | 19.4 | 14.95 |
| | SError | 10.54808039 | 8.42807807 | 10.1231418 | 2.793295545 | 6.650563886 | 4.764504171 |
| | pValue | 0.198202864 | 0.11819731 | 0.123985904 | 0.023885517 | 0.127758283 | 0.089610323 |
| | | | | 10 nmol GLP-1 PEG | | | |
| MJ | 0.0986 | 39.3 | 16.5 | 13.5 | 31.2 | | 13.5 |
| ML | 0.0948 | 13.5 | 36.9 | 48 | 19.2 | | 14.4 |
| MU | 0.0928 | 32.4 | 13.8 | 15.6 | 12 | | 12.3 |
| MY | 0.0964 | 121.2 | 122.7 | 95.1 | 85.8 | 56.1 | 48.3 |
| NB | 0.103 | 35.7 | 50.7 | 56.4 | 34.8 | 13.2 | 16.5 |
| ND | 0.0852 | 70.5 | 56.7 | 63.9 | 21.3 | 10.8 | 7.5 |
| | Ave | 52.1 | 49.55 | 48.75 | 34.05 | 26.7 | 18.75 |
| | StError | 15.73130637 | 16.2621801 | 12.62063786 | 10.88735505 | 14.71631747 | 6.035768385 |
| | pValue | 0.033003008 | 0.03509872 | 0.014767024 | 0.034608806 | 0.24535686 | 0.069087455 |
| | | 0 | 15 | 30 | 60 | 90 | 120 |
| Vehicle | Ave | 5.45 | 2.85 | 2.7 | 2.7 | 3 | 4.4 |
| 3 nmol | Ave | 21.2 | 18.75 | 21.4 | 11.65 | 19.4 | 14.95 |
| 10 nmol | Ave | 52.1 | 49.55 | 48.75 | 34.05 | 26.7 | 18.75 |

| Mouse ID | Dose | Time 0 Actual C-Peptide | Time 15 Actual C-Peptide | Time 30 Actual C-Peptide | Time 60 Actual C-Peptide | Time 90 Actual C-Peptide | Time 120 Actual C-Peptide |
|---|---|---|---|---|---|---|---|
| | | | | Vehicle | | | |
| MR | 0.0994 | 2127 | 1188 | 1167 | 1182 | | 2736 |
| MS | 0.0938 | 3243 | 1875 | 1992 | 2709 | | 5643 |
| MZ | 0.097 | 1857 | 1266 | 1392 | 1533 | | 2916 |
| NA | 0.0942 | 3666 | 2571 | 2322 | 2082 | 1932 | 3051 |
| NI | 0.0936 | 2391 | 2178 | 1776 | 2181 | 2469 | 3777 |
| NK | 0.0974 | 2580 | 2517 | 2115 | 2577 | 2910 | 4695 |
| | Ave | 2644 | 1932.5 | 1794 | 2044 | 2437 | 3803 |
| | StError | 280.3597689 | 245.7235235 | 180.3779366 | 241.5706936 | 282.7772975 | 471.6178538 |
| | | | | 3 nmol GLP-1 PEG | | | |
| MO | 0.0988 | | 2130 | 3492 | 2613 | | 1989 |
| MP | 0.0914 | 2472 | 5445 | 4632 | 4326 | | 4248 |
| MT | 0.1066 | 2577 | 2919 | 2802 | 4149 | | 3027 |
| NC | 0.0998 | 9663 | 10278 | | 6759 | 7197 | 9849 |
| NE | 0.1006 | 6726 | 5349 | 6747 | | 3843 | 9855 |
| NG | 0.099 | 5010 | 4812 | 3975 | 5670 | 6390 | 8337 |
| | Ave | 5289.6 | 5155.5 | 4329.6 | 4703.4 | 5810 | 6217.5 |
| | StError | 1234.320279 | 1163.8275 | 615.6346725 | 644.8310244 | 1010.714104 | 1447.410464 |
| | pValue | 0.104283454 | 0.021669546 | 0.012956014 | 0.010105544 | 0.095491566 | 0.15910403 |
| | | | | 10 nmol GLP-1 PEG | | | |
| MJ | 0.0986 | 7200 | 3501 | 4296 | 10332 | | 5901 |
| ML | 0.0948 | 3687 | 8049 | 9627 | | | 4821 |
| MU | 0.0928 | 5955 | | 6300 | | | 7278 |
| MY | 0.0964 | 16212 | 17643 | 13266 | 12423 | 11124 | 11943 |
| NB | 0.103 | 8139 | 9174 | 11262 | 7170 | 4362 | 6954 |
| ND | 0.0852 | 12162 | 8478 | 10785 | 4947 | 3867 | 4506.5 |
| | Ave | 8892.5 | 9369 | 9256 | 8718 | 6451 | 6900.5 |
| | StError | 1856.727996 | 2096.294409 | 1365.273526 | 1352.954914 | 2340.865438 | 1104.975497 |
| | pValue | 0.015654599 | 0.025508262 | 0.001556618 | 0.035883718 | 0.263009115 | 0.082555028 |
| | | 0 | 15 | 30 | 60 | 90 | 120 |
| Vehicle | Ave | 2644 | 1932.5 | 1794 | 2044 | 2437 | 3803 |
| 3 nmol | Ave | 5289.6 | 5155.5 | 4329.6 | 4703.4 | 5810 | 6217.5 |
| 10 nmol | Ave | 8892.5 | 9369 | 9256 | 8718 | 6451 | 6900.5 |

We claim:

1. A PEGylated GLP-1 compound comprising the amino acid sequence of Formula IV (SEQ ID NO:6)

Formula IV
(SEQ ID NO: 6)
$Xaa_7$-$Xaa_8$-Glu-Gly-$Xaa_{11}$-$Xaa_{12}$-Thr-Ser-Asp-$Xaa_{16}$-

Ser-$Xaa_{18}$-$Xaa_{19}$-$Xaa_{20}$-Glu-$Xaa_{22}$-$Xaa_{23}$-$Xaa_{24}$-$Xaa_{25}$-

$Xaa_{26}$-$Xaa_{27}$-Phe-Ile-$Xaa_{30}$-Trp-Leu-$Xaa_{33}$-Xaa-$_{34}$-

$Xaa_{35}$-$Xaa_{36}$-$Xaa_{37}$-$Xaa_{38}$-$Xaa_{39}$-$Xaa_{40}$-$Xaa_{41}$-$Xaa_{42}$-

$Xaa_{43}$-$Xaa_{44}$-$Xaa_{45}$-$Xaa_{46}$-$Xaa_{47}$ wherein:
$Xaa_7$ is: L-histidine, D-histidine, desamino-histidine, 2-amino-histidine, β-hydroxy-histidine, homohistidine, α-fluoromethyl-histidine, or α-methyl-histidine;
$Xaa_8$ is: Ala, Gly, Val, Leu, Ile, Ser, or Thr;
$Xaa_{11}$ is: Thr or Cys
$Xaa_{12}$ is: Phe, Trp, Tyr, or Cys;
$Xaa_{16}$ is: Val, Trp, Ile, Len, Phe, Tyr, or Cys;
$Xaa_{18}$ is: Ser, Trp, Tyr, Phe, Lys, Ile, Leu, Val;
$Xaa_{19}$ is: Tyr, Trp, or Phe;
$Xaa_{20}$ is: Leu, Phe, Tyr, or Trp;
$Xaa_{22}$ is: Gly, Gln, Asp, Lys or Cys;
$Xaa_{23}$ is: Gln or Cys;
$Xaa_{24}$ is: Ala or Cys;
$Xaa_{25}$ is: Ala, Val, Be, Leu, or Cys;
$Xaa_{26}$ is: Lys or Cys;
$Xaa_{27}$ is: Gln, Be, Ala, or Cys;
$Xaa_{30}$ is: Ala, Gln or Cys
$Xaa_{33}$ is: Val or Ile;
$Xaa_{34}$ is: Lys, Asp, Arg, Glu or Cys;
$Xaa_{35}$ is: Gly or Cys;
$Xaa_{36}$ is: Gly, Pro, Arg or Cys;
$Xaa_{37}$ is: Gly, Pro, Ser or Cys;
$Xaa_{38}$ is: Ser, Pro, His or Cys;
$Xaa_{39}$ is: Ser, Arg, Thr, Trp, Lys or Cys;
$Xaa_{40}$ is: Ser, Gly, or Cys;
$Xaa_{41}$ is: Ala, Asp, Arg, Glu, Lys, Gly, or Cys;
$Xaa_{42}$ is: Pro, Ala, Cys, $NH_2$, or is absent;
$Xaa_{43}$ is: Pro, Ala, Cys, $NH_2$, or is absent;
$Xaa_{44}$ is: Pro, Ala, Arg, Lys, His, Cys, $NH_2$, or is absent;
$Xaa_{45}$ is: Ser, His, Pro, Lys, Arg, Cys, $NH_2$ or is absent;
$Xaa_{46}$ is: His, Ser, Arg, Lys, Cys, $NH_2$ or is absent; and
$Xaa_{47}$ is: His, Ser, Arg, Lys, Cys, $NH_2$ or is absent;
and wherein:
at least one Cys residue is covalently attached to a PEG molecule, and provided that if $Xaa_{42}$, $Xaa_{43}$, $Xaa_{44}$, $Xaa_{45}$ or $Xaa_{46}$ is absent each amino acid downstream is absent;
and provided that there are no more than two Cys residues in the molecule.

2. The PEGylated GLP-1 compound of claim 1, provided that the PEGylated GLP-1 compound does not differ from GLP-1(7-37)OH or GLP-1(7-36)$NH_2$ by more than 7 amino acids within the amino acids from 7-37.

3. The PEGylated GLP-1 compound of claim 1, provided that the PEGylated GLP-1 compound does not differ from GLP-1(7-37)OH or GLP-1(7-36)$NH_2$ by more than 6 amino acids within the amino acids from 7-37.

4. The PEGylated GLP-1 compound of claim 1, provided that the PEGylated GLP-1 compound does not differ from GLP-1(7-37)OH or GLP-1(7-36)$NH_2$ by more than 5 amino acids within the amino acids from 7-37.

5. The PEGylated GLP-1 compound of claim 1, provided that the PEGylated GLP-1 compound does not differ from GLP-1(7-37)OH or GLP-1(7-36)$NH_2$ by more than 4 amino acids within the amino acids from 7-37.

6. The PEGylated GLP-1 compound of claim 1, provided that the PEGylated GLP-1 compound does not differ from GLP-1(7-37)OH or GLP-1(7-36)$NH_2$ by more than 3 amino acids within the amino acids from 7-37.

7. A method of treating a subject suffering from diabetes, obesity, stroke, myocardial infarction, irritable bowel syndrome or functional dyspepsia comprising administering to the subject an effective amount of a PEGylated GLP-1 compound of any one of claims 1-6.

8. The method of claim 7 wherein the subject is suffering from diabetes.

9. The method of claim 8 wherein the diabetes is non-insulin dependent diabetes.

10. The method of claim 7 wherein the subject is suffering from obesity.

* * * * *

UNITED STATES PATENT AND TRADEMARK OFFICE
CERTIFICATE OF CORRECTION

| | | |
|---|---|---|
| PATENT NO. | : 7,557,183 B2 | Page 1 of 1 |
| APPLICATION NO. | : 10/548328 | |
| DATED | : July 7, 2009 | |
| INVENTOR(S) | : DiMarchi et al. | |

It is certified that error appears in the above-identified patent and that said Letters Patent is hereby corrected as shown below:

In Column 63, Line 39, Claim 1, delete "Len" and insert -- Leu --, therefor.

In Column 63, Line 43, Claim 1, delete "Gln" and insert -- Glu --, therefor.

In Column 63, Line 46, Claim 1, delete "Be" and insert -- Ile --, therefor.

In Column 63, Line 48, Claim 1, delete "Gln, Be," and insert -- Glu, Ile, --, therefor.

In Column 63, Line 49, Claim 1, delete "Gln" and insert -- Glu --, therefor.

Signed and Sealed this

Twenty-sixth Day of January, 2010

David J. Kappos
*Director of the United States Patent and Trademark Office*

SEQUENCE LISTING

<160> NUMBER OF SEQ ID NOS: 10

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 30
<212> TYPE: PRT
<213> ORGANISM: Homo sapiens

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is L-histidine, D-histidine,
      desamino-histidine, 2-amino-histidine, beta-hydroxy-histidine,
      homohistidine, alpha-fluoromethyl-histidine, or alpha
      methyl-histidine
<220> FEATURE:
<221> NAME/KEY: MISC_FEATURE
<222> LOCATION: (2)..(2)
<223> OTHER INFORMATION: Xaa at position 2 is Ala, Gly, Val, Leu, Ile,
      Ser, or Thr
<220> FEATURE:
<221> NAME/KEY: MISC_FEATURE
<222> LOCATION: (5)..(5)
<223> OTHER INFORMATION: Xaa at position 5 is Thr or Cys
<220> FEATURE:
<221> NAME/KEY: MISC_FEATURE
<222> LOCATION: (6)..(6)
<223> OTHER INFORMATION: Xaa at position 6 is Phe, Trp, Tyr, or Cys
<220> FEATURE:
<221> NAME/KEY: MISC_FEATURE
<222> LOCATION: (10)..(10)
<223> OTHER INFORMATION: Xaa at position 10 is Val, Trp, Ile, Leu, Phe,
      Tyr, or Cys
<220> FEATURE:
<221> NAME/KEY: MISC_FEATURE
<222> LOCATION: (12)..(12)
<223> OTHER INFORMATION: Xaa at position 12 is Ser, Trp, Tyr, Phe, Lys,
      Ile, Leu, or Val
<220> FEATURE:
<221> NAME/KEY: MISC_FEATURE
<222> LOCATION: (13)..(13)
<223> OTHER INFORMATION: Xaa at position 13 is Tyr, Trp, or Phe
<220> FEATURE:
<221> NAME/KEY: MISC_FEATURE
<222> LOCATION: (14)..(14)
<223> OTHER INFORMATION: Xaa at position 14 is Leu, Phe, Tyr, or Trp
<220> FEATURE:
<221> NAME/KEY: MISC_FEATURE

```
<222> LOCATION: (16)..(16)
<223> OTHER INFORMATION: Xaa at position 16 is Gly, Glu, Asp, Lys, or
      Cys
<220> FEATURE:
<221> NAME/KEY: MISC_FEATURE
<222> LOCATION: (17)..(17)
<223> OTHER INFORMATION: Xaa at position 17 is Gln or Cys
<220> FEATURE:
<221> NAME/KEY: MISC_FEATURE
<222> LOCATION: (18)..(18)
<223> OTHER INFORMATION: Xaa at position 18 is Ala or Cys
<220> FEATURE:
<221> NAME/KEY: MISC_FEATURE
<222> LOCATION: (19)..(19)
<223> OTHER INFORMATION: Xaa at position 19 is Ala, Val, Ile, Leu, or
      Cys
<220> FEATURE:
<221> NAME/KEY: MISC_FEATURE
<222> LOCATION: (20)..(20)
<223> OTHER INFORMATION: Xaa at position 20 is Lys or Cys
<220> FEATURE:
<221> NAME/KEY: MISC_FEATURE
<222> LOCATION: (21)..(21)
<223> OTHER INFORMATION: Xaa at position 21 is Glu, Ile, Ala, or Cys
<220> FEATURE:
<221> NAME/KEY: MISC_FEATURE
<222> LOCATION: (24)..(24)
<223> OTHER INFORMATION: Xaa at position 24 is Ala, Glu, or Cys
<220> FEATURE:
<221> NAME/KEY: MISC_FEATURE
<222> LOCATION: (27)..(27)
<223> OTHER INFORMATION: Xaa at position 27 is Val or Ile
<220> FEATURE:
<221> NAME/KEY: MISC_FEATURE
<222> LOCATION: (28)..(28)
<223> OTHER INFORMATION: Xaa at position 28 is Lys or Cys
<220> FEATURE:
<221> NAME/KEY: MISC_FEATURE
<222> LOCATION: (29)..(29)
<223> OTHER INFORMATION: Xaa at position 29 is Gly or Cys
<220> FEATURE:
<221> NAME/KEY: MISC_FEATURE
<222> LOCATION: (30)..(30)
<223> OTHER INFORMATION: Xaa at position 30 is Arg or Cys
<220> FEATURE:
<221> NAME/KEY: MISC_FEATURE
<222> LOCATION: (31)..(31)
<223> OTHER INFORMATION: Xaa at position 31 is Gly, His, Cys, Absent, or
      a Modified Residue
<220> FEATURE:
<221> NAME/KEY: MOD_RES
<222> LOCATION: (31)..(31)
<223> OTHER INFORMATION: AMIDATION

<400> SEQUENCE: 3

Xaa Xaa Glu Gly Xaa Xaa Thr Ser Asp Xaa Ser Xaa Xaa Xaa Glu Xaa
1               5                   10                  15

Xaa Xaa Xaa Xaa Xaa Phe Ile Xaa Trp Leu Xaa Xaa Xaa Xaa Xaa
            20                  25                  30

<210> SEQ ID NO 4
<211> LENGTH: 31
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is L-histidine, D-histidine,
      desamino-histidine, 2-amino-histidine, beta-hydroxy-histidine,
      homohistidine, alpha-fluoromethyl-histidine, or
      alpha-methyl-histidine
<220> FEATURE:
<221> NAME/KEY: MISC_FEATURE
<222> LOCATION: (2)..(2)
```

```
<223> OTHER INFORMATION: Xaa at position 2 is Gly, Ala, Val, Leu, Ile,
      Ser, or Thr
<220> FEATURE:
<221> NAME/KEY: MISC_FEATURE
<222> LOCATION: (5)..(5)
<223> OTHER INFORMATION: Xaa at position 5 is Thr or Cys
<220> FEATURE:
<221> NAME/KEY: MISC_FEATURE
<222> LOCATION: (6)..(6)
<223> OTHER INFORMATION: Xaa at position 6 is Phe or Cys
<220> FEATURE:
<221> NAME/KEY: MISC_FEATURE
<222> LOCATION: (10)..(10)
<223> OTHER INFORMATION: Xaa at position 10 is Val, Phe, Tyr, Trp, or
      Cys
<220> FEATURE:
<221> NAME/KEY: MISC_FEATURE
<222> LOCATION: (12)..(12)
<223> OTHER INFORMATION: Xaa at position 12 is Ser, Tyr, Trp, Phe, Lys,
      Ile, Leu, or Val
<220> FEATURE:
<221> NAME/KEY: MISC_FEATURE
<222> LOCATION: (16)..(16)
<223> OTHER INFORMATION: Xaa at position 16 is Gly, Glu, Asp, Lys, or
      Cys
<220> FEATURE:
<221> NAME/KEY: MISC_FEATURE
<222> LOCATION: (17)..(17)
<223> OTHER INFORMATION: Xaa at position 17 is Gln or Cys
<220> FEATURE:
<221> NAME/KEY: MISC_FEATURE
<222> LOCATION: (18)..(18)
<223> OTHER INFORMATION: Xaa at position 18 is Ala or Cys
<220> FEATURE:
<221> NAME/KEY: MISC_FEATURE
<222> LOCATION: (19)..(19)
<223> OTHER INFORMATION: Xaa at position 19 is Ala, Val, Ile, Leu, or
      Cys
<220> FEATURE:
<221> NAME/KEY: MISC_FEATURE
<222> LOCATION: (20)..(20)
<223> OTHER INFORMATION: Xaa at position 20 is Lys or Cys
<220> FEATURE:
<221> NAME/KEY: MISC_FEATURE
<222> LOCATION: (21)..(21)
<223> OTHER INFORMATION: Xaa at position 21 is Glu or Cys
<220> FEATURE:
<221> NAME/KEY: MISC_FEATURE
<222> LOCATION: (24)..(24)
<223> OTHER INFORMATION: Xaa at position 24 is Ala or Cys
<220> FEATURE:
<221> NAME/KEY: MISC_FEATURE
<222> LOCATION: (27)..(27)
<223> OTHER INFORMATION: Xaa at position 27 is Val or Ile
<220> FEATURE:
<221> NAME/KEY: MISC_FEATURE
<222> LOCATION: (28)..(28)
<223> OTHER INFORMATION: Xaa at position 28 is Lys or Cys
<220> FEATURE:
<221> NAME/KEY: MISC_FEATURE
<222> LOCATION: (29)..(29)
<223> OTHER INFORMATION: Xaa at position 29 is Gly or Cys
<220> FEATURE:
<221> NAME/KEY: MISC_FEATURE
<222> LOCATION: (30)..(30)
<223> OTHER INFORMATION: Xaa at position 30 is Arg or Cys
<220> FEATURE:
<221> NAME/KEY: MISC_FEATURE
<222> LOCATION: (31)..(31)
<223> OTHER INFORMATION: Xaa at position 31 is Gly, Cys, Absent, or a
      Modified Residue
<220> FEATURE:
<221> NAME/KEY: MOD_RES
<222> LOCATION: (31)..(31)
<223> OTHER INFORMATION: AMIDATION

<400> SEQUENCE: 4

Xaa Xaa Glu Gly Xaa Xaa Thr Ser Asp Xaa Ser Xaa Tyr Leu Glu Xaa
```

-continued

```
      1               5                  10                 15
Xaa Xaa Xaa Xaa Xaa Phe Ile Xaa Trp Leu Xaa Xaa Xaa Xaa Xaa
                20                  25                 30

<210> SEQ ID NO 5
<211> LENGTH: 44
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is L-histidine, D-histidine,
      desamino-histidine, 2-amino-histidine, beta-hydroxy-histidine,
      homohistidine, alpha-fluoromethyl-histidine, or
      alpha-methyl-histidine
<220> FEATURE:
<221> NAME/KEY: MISC_FEATURE
<222> LOCATION: (2)..(2)
<223> OTHER INFORMATION: Xaa at position 2 is Ala, Gly, Val, Leu, Ile,
      Ser, or Thr
<220> FEATURE:
<221> NAME/KEY: MISC_FEATURE
<222> LOCATION: (5)..(5)
<223> OTHER INFORMATION: Xaa at position 5 is Thr or Cys
<220> FEATURE:
<221> NAME/KEY: MISC_FEATURE
<222> LOCATION: (6)..(6)
<223> OTHER INFORMATION: Xaa at position 6 is Phe, Trp, Tyr, or Cys
<220> FEATURE:
<221> NAME/KEY: MISC_FEATURE
<222> LOCATION: (10)..(10)
<223> OTHER INFORMATION: Xaa at position 10 is Val, Trp, Ile, Leu, Phe,
      Tyr, or Cys
<220> FEATURE:
<221> NAME/KEY: MISC_FEATURE
<222> LOCATION: (12)..(12)
<223> OTHER INFORMATION: Xaa at position 12 is Ser, Trp, Tyr, Phe, Lys,
      Ile, Leu, or Val
<220> FEATURE:
<221> NAME/KEY: MISC_FEATURE
<222> LOCATION: (13)..(13)
<223> OTHER INFORMATION: Xaa at position 13 is Tyr, Trp, or Phe
<220> FEATURE:
<221> NAME/KEY: MISC_FEATURE
<222> LOCATION: (14)..(14)
<223> OTHER INFORMATION: Xaa at position 14 is Leu, Phe, Tyr, or Trp
<220> FEATURE:
<221> NAME/KEY: MISC_FEATURE
<222> LOCATION: (16)..(16)
<223> OTHER INFORMATION: Xaa at position 16 is Gly, Glu, Asp, Lys, or
      Cys
<220> FEATURE:
<221> NAME/KEY: MISC_FEATURE
<222> LOCATION: (17)..(17)
<223> OTHER INFORMATION: Xaa at position 17 is Gln or Cys
<220> FEATURE:
<221> NAME/KEY: MISC_FEATURE
<222> LOCATION: (18)..(18)
<223> OTHER INFORMATION: Xaa at position 18 is Ala or Cys
<220> FEATURE:
<221> NAME/KEY: MISC_FEATURE
<222> LOCATION: (19)..(19)
<223> OTHER INFORMATION: Xaa at position 19 is Ala, Val, Ile, Leu, or
      Cys
<220> FEATURE:
<221> NAME/KEY: MISC_FEATURE
<222> LOCATION: (20)..(20)
<223> OTHER INFORMATION: Xaa at position 20 is Lys or Cys
<220> FEATURE:
<221> NAME/KEY: MISC_FEATURE
<222> LOCATION: (21)..(21)
<223> OTHER INFORMATION: Xaa at position 21 is Glu, Ile, Ala, or Cys
<220> FEATURE:
<221> NAME/KEY: MISC_FEATURE
<222> LOCATION: (24)..(24)
```

```
<223> OTHER INFORMATION: Xaa at position 24 is Ala, Glu, or Cys
<220> FEATURE:
<221> NAME/KEY: MISC_FEATURE
<222> LOCATION: (27)..(27)
<223> OTHER INFORMATION: Xaa at position 27 is Val or Ile
<220> FEATURE:
<221> NAME/KEY: MISC_FEATURE
<222> LOCATION: (28)..(28)
<223> OTHER INFORMATION: Xaa at position 28 is Lys,Asp, Arg, Glu, or Cys
<220> FEATURE:
<221> NAME/KEY: MISC_FEATURE
<222> LOCATION: (29)..(29)
<223> OTHER INFORMATION: Xaa at position 29 is Gly or Cys
<220> FEATURE:
<221> NAME/KEY: MISC_FEATURE
<222> LOCATION: (30)..(30)
<223> OTHER INFORMATION: Xaa at position 30 is Gly, Pro, Arg, or Cys
<220> FEATURE:
<221> NAME/KEY: MISC_FEATURE
<222> LOCATION: (31)..(31)
<223> OTHER INFORMATION: Xaa at position 31 is Gly, Pro, Ser, or Cys
<220> FEATURE:
<221> NAME/KEY: MISC_FEATURE
<222> LOCATION: (32)..(32)
<223> OTHER INFORMATION: Xaa at position 32 is Ser, Pro, His or Cys
<220> FEATURE:
<221> NAME/KEY: MISC_FEATURE
<222> LOCATION: (33)..(33)
<223> OTHER INFORMATION: Xaa at position 33 is Ser, Arg, Thr, Trp, Lys,
      or Cys
<220> FEATURE:
<221> NAME/KEY: MISC_FEATURE
<222> LOCATION: (34)..(34)
<223> OTHER INFORMATION: Xaa at position 34 is Ser, Gly, or Cys
<220> FEATURE:
<221> NAME/KEY: MISC_FEATURE
<222> LOCATION: (35)..(35)
<223> OTHER INFORMATION: Xaa at position 35 is Ala, Asp, Arg, Glu, Lys,
      Gly, or Cys
<220> FEATURE:
<221> NAME/KEY: MISC_FEATURE
<222> LOCATION: (36)..(36)
<223> OTHER INFORMATION: Xaa at position 36 is Pro, Ala, Cys, Absent, or
      a Modified
      Residue
<220> FEATURE:
<221> NAME/KEY: MOD_RES
<222> LOCATION: (36)..(36)
<223> OTHER INFORMATION: AMIDATION
<220> FEATURE:
<221> NAME/KEY: MISC_FEATURE
<222> LOCATION: (37)..(37)
<223> OTHER INFORMATION: Xaa at position 37 is Pro, Ala, Cys, Absent, or
      a Modified
      Residue
<220> FEATURE:
<221> NAME/KEY: MOD_RES
<222> LOCATION: (37)..(37)
<223> OTHER INFORMATION: AMIDATION
<220> FEATURE:
<221> NAME/KEY: MISC_FEATURE
<222> LOCATION: (38)..(38)
<223> OTHER INFORMATION: Xaa at position 38 is Pro, Ala, Arg, Lys, His,
      Cys, Absent, or a
      Modified Residue
<220> FEATURE:
<221> NAME/KEY: MOD_RES
<222> LOCATION: (38)..(38)
<223> OTHER INFORMATION: AMIDATION
<220> FEATURE:
<221> NAME/KEY: MISC_FEATURE
<222> LOCATION: (39)..(39)
<223> OTHER INFORMATION: Xaa at position 39 is Ser, His, Pro, Lys, Arg,
      Gly, Cys, Absent, or a Modified Residue
<220> FEATURE:
<221> NAME/KEY: MOD_RES
<222> LOCATION: (39)..(39)
<223> OTHER INFORMATION: AMIDATION
<220> FEATURE:
```

```
<221> NAME/KEY: MISC_FEATURE
<222> LOCATION: (40)..(40)
<223> OTHER INFORMATION: Xaa at position 40 is His, Ser, Arg, Lys, Pro,
      Gly, Cys, Absent, or a Modified Residue
<220> FEATURE:
<221> NAME/KEY: MOD_RES
<222> LOCATION: (40)..(40)
<223> OTHER INFORMATION: AMIDATION
<220> FEATURE:
<221> NAME/KEY: MISC_FEATURE
<222> LOCATION: (41)..(41)
<223> OTHER INFORMATION: Xaa at position 41 is His, Ser, Arg, Lys, Cys,
      Absent, or a Modified Residue
<220> FEATURE:
<221> NAME/KEY: MOD_RES
<222> LOCATION: (41)..(41)
<223> OTHER INFORMATION: AMIDATION
<220> FEATURE:
<221> NAME/KEY: MISC_FEATURE
<222> LOCATION: (42)..(42)
<223> OTHER INFORMATION: Xaa at position 42 is Gly, His, Cys, Absent, or
      a Modified Residue
<220> FEATURE:
<221> NAME/KEY: MOD_RES
<222> LOCATION: (42)..(42)
<223> OTHER INFORMATION: AMIDATION
<220> FEATURE:
<221> NAME/KEY: MISC_FEATURE
<222> LOCATION: (43)..(43)
<223> OTHER INFORMATION: Xaa at position 43 is Pro, His, Cys, Absent, or
      a Modified Residue
<220> FEATURE:
<221> NAME/KEY: MOD_RES
<222> LOCATION: (43)..(43)
<223> OTHER INFORMATION: AMIDATION
<220> FEATURE:
<221> NAME/KEY: MISC_FEATURE
<222> LOCATION: (44)..(44)
<223> OTHER INFORMATION: Xaa at position 44 is Ser, His, Cys, Absent, or
      a Modified Residue
<220> FEATURE:
<221> NAME/KEY: MOD_RES
<222> LOCATION: (44)..(44)
<223> OTHER INFORMATION: AMIDATION

<400> SEQUENCE: 5

Xaa Xaa Glu Gly Xaa Xaa Thr Ser Asp Xaa Ser Xaa Xaa Xaa Glu Xaa
1               5                   10                  15

Xaa Xaa Xaa Xaa Xaa Phe Ile Xaa Trp Leu Xaa Xaa Xaa Xaa Xaa Xaa
            20                  25                  30

Xaa Xaa Xaa Xaa Xaa Xaa Xaa Xaa Xaa Xaa Xaa Xaa
        35                  40

<210> SEQ ID NO 6
<211> LENGTH: 41
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is L-histidine, D-histidine,
      desamino-histidine, 2-amino-histidine, beta-hydroxy-histidine,
      homohistidine, alpha-fluoromethyl-histidine, or
      alpha-methyl-histidine
<220> FEATURE:
<221> NAME/KEY: MISC_FEATURE
<222> LOCATION: (2)..(2)
<223> OTHER INFORMATION: Xaa at position 2 is Ala, Gly, Val, Leu, Ile,
      Ser, or Thr
<220> FEATURE:
<221> NAME/KEY: MISC_FEATURE
<222> LOCATION: (5)..(5)
<223> OTHER INFORMATION: Xaa at position 5 is Thr or Cys
```

```
<220> FEATURE:
<221> NAME/KEY: MISC_FEATURE
<222> LOCATION: (6)..(6)
<223> OTHER INFORMATION: Xaa at position 6 is Phe, Trp, Tyr, or Cys
<220> FEATURE:
<221> NAME/KEY: MISC_FEATURE
<222> LOCATION: (10)..(10)
<223> OTHER INFORMATION: Xaa at position 10 is Val, Trp, Ile, Leu, Phe,
      Tyr, or Cys
<220> FEATURE:
<221> NAME/KEY: MISC_FEATURE
<222> LOCATION: (12)..(12)
<223> OTHER INFORMATION: Xaa at position 12 is Ser, Trp, Tyr, Phe, Lys,
      Ile, Leu, Val
<220> FEATURE:
<221> NAME/KEY: MISC_FEATURE
<222> LOCATION: (13)..(13)
<223> OTHER INFORMATION: Xaa at position 13 is Tyr, Trp, or Phe
<220> FEATURE:
<221> NAME/KEY: MISC_FEATURE
<222> LOCATION: (14)..(14)
<223> OTHER INFORMATION: Xaa at position 14 is Leu, Phe, Tyr, or Trp
<220> FEATURE:
<221> NAME/KEY: MISC_FEATURE
<222> LOCATION: (16)..(16)
<223> OTHER INFORMATION: Xaa at position 16 is Gly, Glu, Asp, Lys or Cys
<220> FEATURE:
<221> NAME/KEY: MISC_FEATURE
<222> LOCATION: (17)..(17)
<223> OTHER INFORMATION: Xaa at position 17 is Gln or Cys
<220> FEATURE:
<221> NAME/KEY: MISC_FEATURE
<222> LOCATION: (18)..(18)
<223> OTHER INFORMATION: Xaa at position 18 is Ala or Cys
<220> FEATURE:
<221> NAME/KEY: MISC_FEATURE
<222> LOCATION: (19)..(19)
<223> OTHER INFORMATION: Xaa at position 19 is Ala, Val, Ile, Leu, or
      Cys
<220> FEATURE:
<221> NAME/KEY: MISC_FEATURE
<222> LOCATION: (20)..(20)
<223> OTHER INFORMATION: Xaa at position 20 is Lys or Cys
<220> FEATURE:
<221> NAME/KEY: MISC_FEATURE
<222> LOCATION: (21)..(21)
<223> OTHER INFORMATION: Xaa at position 21 is Glu, Ile, Ala, or Cys
<220> FEATURE:
<221> NAME/KEY: MISC_FEATURE
<222> LOCATION: (24)..(24)
<223> OTHER INFORMATION: Xaa at position 24 is Ala, Glu or Cys
<220> FEATURE:
<221> NAME/KEY: MISC_FEATURE
<222> LOCATION: (27)..(27)
<223> OTHER INFORMATION: Xaa at position 27 is Val or Ile
<220> FEATURE:
<221> NAME/KEY: MISC_FEATURE
<222> LOCATION: (28)..(28)
<223> OTHER INFORMATION: Xaa at position 28 is Lys, Asp, Arg, Glu, or
      Cys
<220> FEATURE:
<221> NAME/KEY: MISC_FEATURE
<222> LOCATION: (29)..(29)
<223> OTHER INFORMATION: Xaa at position 29 is Gly or Cys
<220> FEATURE:
<221> NAME/KEY: MISC_FEATURE
<222> LOCATION: (30)..(30)
<223> OTHER INFORMATION: Xaa at position 30 is Gly, Pro, Arg, or Cys
<220> FEATURE:
<221> NAME/KEY: MISC_FEATURE
<222> LOCATION: (31)..(31)
<223> OTHER INFORMATION: Xaa at position 31 Gly, Pro, Ser, or Cys
<220> FEATURE:
<221> NAME/KEY: MISC_FEATURE
<222> LOCATION: (32)..(32)
<223> OTHER INFORMATION: Xaa at position 32 is Ser, Pro, His, or Cys
<220> FEATURE:
<221> NAME/KEY: MISC_FEATURE
<222> LOCATION: (33)..(33)
```

```
<223> OTHER INFORMATION: Xaa at position 33 is Ser, Arg, Thr, Trp, Lys,
      or Cys
<220> FEATURE:
<221> NAME/KEY: MISC_FEATURE
<222> LOCATION: (34)..(34)
<223> OTHER INFORMATION: Xaa at position 34 is Ser, Gly, or Cys
<220> FEATURE:
<221> NAME/KEY: MISC_FEATURE
<222> LOCATION: (35)..(35)
<223> OTHER INFORMATION: Xaa at position 35 is Ala, Asp, Arg, Glu, Lys,
      Gly, or Cys
<220> FEATURE:
<221> NAME/KEY: MISC_FEATURE
<222> LOCATION: (36)..(36)
<223> OTHER INFORMATION: Xaa at position 36 is Pro, Ala, Cys, Absent, or
      a Modified
      Residue
<220> FEATURE:
<221> NAME/KEY: MOD_RES
<222> LOCATION: (36)..(36)
<223> OTHER INFORMATION: AMIDATION
<220> FEATURE:
<221> NAME/KEY: MISC_FEATURE
<222> LOCATION: (37)..(37)
<223> OTHER INFORMATION: Xaa at position 37 is Pro, Ala, Cys, Absent, or
      a Modified
      Residue
<220> FEATURE:
<221> NAME/KEY: MOD_RES
<222> LOCATION: (37)..(37)
<223> OTHER INFORMATION: AMIDATION
<220> FEATURE:
<221> NAME/KEY: MISC_FEATURE
<222> LOCATION: (38)..(38)
<223> OTHER INFORMATION: Xaa at position 38 is Pro, Ala, Arg, Lys, His,
      Cys, Absent, or a
      Modified Residue
<220> FEATURE:
<221> NAME/KEY: MOD_RES
<222> LOCATION: (38)..(38)
<223> OTHER INFORMATION: AMIDATION
<220> FEATURE:
<221> NAME/KEY: MISC_FEATURE
<222> LOCATION: (39)..(39)
<223> OTHER INFORMATION: Xaa at position 39 is Ser, His, Pro, Lys, Arg,
      Cys, Absent, or a
      Modified Residue
<220> FEATURE:
<221> NAME/KEY: MOD_RES
<222> LOCATION: (39)..(39)
<223> OTHER INFORMATION: AMIDATION
<220> FEATURE:
<221> NAME/KEY: MISC_FEATURE
<222> LOCATION: (40)..(40)
<223> OTHER INFORMATION: Xaa at position 40 is His, Ser, Arg, Lys, Cys,
      Absent, or a
      Modified Residue
<220> FEATURE:
<221> NAME/KEY: MOD_RES
<222> LOCATION: (40)..(40)
<223> OTHER INFORMATION: AMIDATION
<220> FEATURE:
<221> NAME/KEY: MISC_FEATURE
<222> LOCATION: (41)..(41)
<223> OTHER INFORMATION: Xaa at position 41 is His, Ser, Arg, Lys, Cys,
      Absent, or a
      Modified Residue
<220> FEATURE:
<221> NAME/KEY: MOD_RES
<222> LOCATION: (41)..(41)
<223> OTHER INFORMATION: AMIDATION

<400> SEQUENCE: 6

Xaa Xaa Glu Gly Xaa Xaa Thr Ser Asp Xaa Ser Xaa Xaa Xaa Glu Xaa
1               5                   10                  15

Xaa Xaa Xaa Xaa Xaa Phe Ile Xaa Trp Leu Xaa Xaa Xaa Xaa Xaa Xaa
            20                  25                  30
```

```
Xaa Xaa Xaa Xaa Xaa Xaa Xaa Xaa Xaa
        35                  40

<210> SEQ ID NO 7
<211> LENGTH: 41
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is L-histidine, D-histidine,
      desamino-histidine, 2-amino-histidine, beta-hydroxy-histidine,
      homohistidine, alpha-fluoromethyl-histidine, or
      alpha-methyl-histidine
<220> FEATURE:
<221> NAME/KEY: MISC_FEATURE
<222> LOCATION: (2)..(2)
<223> OTHER INFORMATION: Xaa at position 2 is Gly, Val, Leu, Ile, Ser,
      or Thr
<220> FEATURE:
<221> NAME/KEY: MISC_FEATURE
<222> LOCATION: (5)..(5)
<223> OTHER INFORMATION: Xaa at position 5 is Thr or Cys
<220> FEATURE:
<221> NAME/KEY: MISC_FEATURE
<222> LOCATION: (6)..(6)
<223> OTHER INFORMATION: Xaa at position 6 is Phe or Cys
<220> FEATURE:
<221> NAME/KEY: MISC_FEATURE
<222> LOCATION: (10)..(10)
<223> OTHER INFORMATION: Xaa at position 10 is Val, Trp, Ile, Leu, Phe,
      Tyr, or Cys
<220> FEATURE:
<221> NAME/KEY: MISC_FEATURE
<222> LOCATION: (16)..(16)
<223> OTHER INFORMATION: Xaa at position 16 is Gly, Glu, Asp, Lys, or
      Cys
<220> FEATURE:
<221> NAME/KEY: MISC_FEATURE
<222> LOCATION: (17)..(17)
<223> OTHER INFORMATION: Xaa at position 17 is Gln or Cys
<220> FEATURE:
<221> NAME/KEY: MISC_FEATURE
<222> LOCATION: (18)..(18)
<223> OTHER INFORMATION: Xaa at position 18 is Ala or Cys
<220> FEATURE:
<221> NAME/KEY: MISC_FEATURE
<222> LOCATION: (19)..(19)
<223> OTHER INFORMATION: Xaa at position 19 is Ala, Val, Ile, Leu, or
      Cys
<220> FEATURE:
<221> NAME/KEY: MISC_FEATURE
<222> LOCATION: (20)..(20)
<223> OTHER INFORMATION: Xaa at position 20 is Lys or Cys
<220> FEATURE:
<221> NAME/KEY: MISC_FEATURE
<222> LOCATION: (21)..(21)
<223> OTHER INFORMATION: Xaa at position 21 is Glu or Cys
<220> FEATURE:
<221> NAME/KEY: MISC_FEATURE
<222> LOCATION: (24)..(24)
<223> OTHER INFORMATION: Xaa at position 24 is Ala or Cys
<220> FEATURE:
<221> NAME/KEY: MISC_FEATURE
<222> LOCATION: (27)..(27)
<223> OTHER INFORMATION: Xaa at position 27 is Val or Ile
<220> FEATURE:
<221> NAME/KEY: MISC_FEATURE
<222> LOCATION: (28)..(28)
<223> OTHER INFORMATION: Xaa at position 28 is Lys, Asp, Arg, Glu, or
      Cys
<220> FEATURE:
<221> NAME/KEY: MISC_FEATURE
<222> LOCATION: (29)..(29)
<223> OTHER INFORMATION: Xaa at position 29 is Gly or Cys
```

```
<220> FEATURE:
<221> NAME/KEY: MISC_FEATURE
<222> LOCATION: (30)..(30)
<223> OTHER INFORMATION: Xaa at position 30 is Gly, Pro, Arg, or Cys
<220> FEATURE:
<221> NAME/KEY: MISC_FEATURE
<222> LOCATION: (31)..(31)
<223> OTHER INFORMATION: Xaa at position 31 is Gly, Pro, Ser, or Cys
<220> FEATURE:
<221> NAME/KEY: MISC_FEATURE
<222> LOCATION: (32)..(32)
<223> OTHER INFORMATION: Xaa at position 32 is Ser, Pro, His, or Cys
<220> FEATURE:
<221> NAME/KEY: MISC_FEATURE
<222> LOCATION: (33)..(33)
<223> OTHER INFORMATION: Xaa at position 33 is Ser, Arg, Thr, Trp, Lys,
      or Cys
<220> FEATURE:
<221> NAME/KEY: MISC_FEATURE
<222> LOCATION: (34)..(34)
<223> OTHER INFORMATION: Xaa at position 34 is Ser, Gly, or Cys
<220> FEATURE:
<221> NAME/KEY: MISC_FEATURE
<222> LOCATION: (35)..(35)
<223> OTHER INFORMATION: Xaa at position 35 is Ala, Asp, Arg, Glu, Lys,
      Gly, or Cys
<220> FEATURE:
<221> NAME/KEY: MISC_FEATURE
<222> LOCATION: (36)..(36)
<223> OTHER INFORMATION: Xaa at position 36 is Pro, Ala, or Cys
<220> FEATURE:
<221> NAME/KEY: MISC_FEATURE
<222> LOCATION: (37)..(37)
<223> OTHER INFORMATION: Xaa at position 37 is Pro, Ala, or Cys
<220> FEATURE:
<221> NAME/KEY: MISC_FEATURE
<222> LOCATION: (38)..(38)
<223> OTHER INFORMATION: Xaa at position 38 is Pro, Ala, Arg, Lys, His
      Cys, Absent, or a
      Modified Residue
<220> FEATURE:
<221> NAME/KEY: MOD_RES
<222> LOCATION: (38)..(38)
<223> OTHER INFORMATION: AMIDATION
<220> FEATURE:
<221> NAME/KEY: MISC_FEATURE
<222> LOCATION: (39)..(39)
<223> OTHER INFORMATION: Xaa at position 39 is Ser, His, Pro, Lys, Arg,
      Cys, Absent or a
      Modified Residue
<220> FEATURE:
<221> NAME/KEY: MOD_RES
<222> LOCATION: (39)..(39)
<223> OTHER INFORMATION: AMIDATION
<220> FEATURE:
<221> NAME/KEY: MISC_FEATURE
<222> LOCATION: (40)..(40)
<223> OTHER INFORMATION: Xaa at position 40 is His, Ser, Arg, Lys, Cys,
      Absent, or a
      Modified Residue
<220> FEATURE:
<221> NAME/KEY: MOD_RES
<222> LOCATION: (40)..(40)
<223> OTHER INFORMATION: AMIDATION
<220> FEATURE:
<221> NAME/KEY: MISC_FEATURE
<222> LOCATION: (41)..(41)
<223> OTHER INFORMATION: Xaa at position 41 is His, Ser, Arg, Lys, Cys,
      Absent, or a
      Modified Residue
<220> FEATURE:
<221> NAME/KEY: MOD_RES
<222> LOCATION: (41)..(41)
<223> OTHER INFORMATION: AMIDATION

<400> SEQUENCE: 7

Xaa Xaa Glu Gly Xaa Xaa Thr Ser Asp Xaa Ser Ser Tyr Lys Glu Xaa
1               5                   10                  15
```

```
Xaa Xaa Xaa Xaa Xaa Phe Ile Xaa Trp Leu Xaa Xaa Xaa Xaa Xaa Xaa
                20              25                  30

Xaa Xaa Xaa Xaa Xaa Xaa Xaa Xaa Xaa
        35                  40

<210> SEQ ID NO 8
<211> LENGTH: 41
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is L-histidine, D-histidine,
      desamino-histidine, 2-amino-histidine, beta-hydroxy-histidine,
      homohistidine, alpha-fluoromethyl-histidine, or
      alpha-methyl-histidine
<220> FEATURE:
<221> NAME/KEY: MISC_FEATURE
<222> LOCATION: (2)..(2)
<223> OTHER INFORMATION: Xaa at position 2 is Gly, Val, Leu, Ile, Ser,
      or Thr
<220> FEATURE:
<221> NAME/KEY: MISC_FEATURE
<222> LOCATION: (5)..(5)
<223> OTHER INFORMATION: Xaa at position 5 is Thr or Cys
<220> FEATURE:
<221> NAME/KEY: MISC_FEATURE
<222> LOCATION: (6)..(6)
<223> OTHER INFORMATION: Xaa at position 6 is Phe or Cys
<220> FEATURE:
<221> NAME/KEY: MISC_FEATURE
<222> LOCATION: (10)..(10)
<223> OTHER INFORMATION: Xaa at position 10 is Val or Cys
<220> FEATURE:
<221> NAME/KEY: MISC_FEATURE
<222> LOCATION: (16)..(16)
<223> OTHER INFORMATION: Xaa at position 16 is Gly, Glu, Asp, Lys or Cys
<220> FEATURE:
<221> NAME/KEY: MISC_FEATURE
<222> LOCATION: (17)..(17)
<223> OTHER INFORMATION: Xaa at position 17 is Gln or Cys
<220> FEATURE:
<221> NAME/KEY: MISC_FEATURE
<222> LOCATION: (18)..(18)
<223> OTHER INFORMATION: Xaa at position 18 is Ala or Cys
<220> FEATURE:
<221> NAME/KEY: MISC_FEATURE
<222> LOCATION: (19)..(19)
<223> OTHER INFORMATION: Xaa at position 19 is Ala, Val, Ile, Leu, or Cys
<220> FEATURE:
<221> NAME/KEY: MISC_FEATURE
<222> LOCATION: (20)..(20)
<223> OTHER INFORMATION: Xaa at position 20 is Lys or Cys
<220> FEATURE:
<221> NAME/KEY: MISC_FEATURE
<222> LOCATION: (21)..(21)
<223> OTHER INFORMATION: Xaa at position 21 is Glu or Cys
<220> FEATURE:
<221> NAME/KEY: MISC_FEATURE
<222> LOCATION: (24)..(24)
<223> OTHER INFORMATION: Xaa at position 24 is Ala or Cys
<220> FEATURE:
<221> NAME/KEY: MISC_FEATURE
<222> LOCATION: (27)..(27)
<223> OTHER INFORMATION: Xaa at position 27 is Val or Ile
<220> FEATURE:
<221> NAME/KEY: MISC_FEATURE
<222> LOCATION: (28)..(28)
<223> OTHER INFORMATION: Xaa at position 28 is Lys or Cys
<220> FEATURE:
<221> NAME/KEY: MISC_FEATURE
<222> LOCATION: (29)..(29)
<223> OTHER INFORMATION: Xaa at position 29 is Gly or Cys
<220> FEATURE:
```

```
<221> NAME/KEY: MISC_FEATURE
<222> LOCATION: (30)..(30)
<223> OTHER INFORMATION: Xaa at position 30 is Gly or Cys
<220> FEATURE:
<221> NAME/KEY: MISC_FEATURE
<222> LOCATION: (31)..(31)
<223> OTHER INFORMATION: Xaa at position 31 is Pro or Cys
<220> FEATURE:
<221> NAME/KEY: MISC_FEATURE
<222> LOCATION: (32)..(32)
<223> OTHER INFORMATION: Xaa at position 32 is Ser, Pro, His, or Cys
<220> FEATURE:
<221> NAME/KEY: MISC_FEATURE
<222> LOCATION: (33)..(33)
<223> OTHER INFORMATION: Xaa at position 33 is Ser, Arg, Thr, Trp, Lys,
      or Cys
<220> FEATURE:
<221> NAME/KEY: MISC_FEATURE
<222> LOCATION: (34)..(34)
<223> OTHER INFORMATION: Xaa at position 34 is Ser, Gly, or Cys
<220> FEATURE:
<221> NAME/KEY: MISC_FEATURE
<222> LOCATION: (35)..(35)
<223> OTHER INFORMATION: Xaa at position 35 is Ala, Asp, Arg, Glu, Lys,
      Gly, or Cys
<220> FEATURE:
<221> NAME/KEY: MISC_FEATURE
<222> LOCATION: (36)..(36)
<223> OTHER INFORMATION: Xaa at position 36 is Pro, Ala, or Cys
<220> FEATURE:
<221> NAME/KEY: MISC_FEATURE
<222> LOCATION: (37)..(37)
<223> OTHER INFORMATION: Xaa at position 37 is Pro, Ala, or Cys
<220> FEATURE:
<221> NAME/KEY: MISC_FEATURE
<222> LOCATION: (38)..(38)
<223> OTHER INFORMATION: Xaa at position 38 is Pro, Ala, Arg, Lys, His,
      Cys, Absent, or a
      Modified Residue
<220> FEATURE:
<221> NAME/KEY: MOD_RES
<222> LOCATION: (38)..(38)
<223> OTHER INFORMATION: AMIDATION
<220> FEATURE:
<221> NAME/KEY: MISC_FEATURE
<222> LOCATION: (39)..(39)
<223> OTHER INFORMATION: Xaa at position 39 is Ser, His, Pro, Lys, Arg,
      Cys, Absent or a
      Modified Residue
<220> FEATURE:
<221> NAME/KEY: MOD_RES
<222> LOCATION: (39)..(39)
<223> OTHER INFORMATION: AMIDATION
<220> FEATURE:
<221> NAME/KEY: MISC_FEATURE
<222> LOCATION: (40)..(40)
<223> OTHER INFORMATION: Xaa at position 40 is His, Ser, Arg, Lys, Cys,
      Absent, or a
      Modified Residue
<220> FEATURE:
<221> NAME/KEY: MOD_RES
<222> LOCATION: (40)..(40)
<223> OTHER INFORMATION: AMIDATION
<220> FEATURE:
<221> NAME/KEY: MISC_FEATURE
<222> LOCATION: (41)..(41)
<223> OTHER INFORMATION: Xaa at position 41 is His, Ser, Arg, Lys, Cys,
      Absent, or a
      Modified Residue
<220> FEATURE:
<221> NAME/KEY: MOD_RES
<222> LOCATION: (41)..(41)
<223> OTHER INFORMATION: AMIDATION

<400> SEQUENCE: 8

Xaa Xaa Glu Gly Xaa Xaa Thr Ser Asp Xaa Ser Ser Tyr Lys Glu Xaa
1               5                   10                  15
```

```
Xaa Xaa Xaa Xaa Xaa Phe Ile Xaa Trp Leu Xaa Xaa Xaa Xaa Xaa Xaa
                20              25                  30

Xaa Xaa Xaa Xaa Xaa Xaa Xaa Xaa Xaa
        35                  40

<210> SEQ ID NO 9
<211> LENGTH: 44
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa at position 5 is Thr or Cys
<220> FEATURE:
<221> NAME/KEY: MISC_FEATURE
<222> LOCATION: (6)..(6)
<223> OTHER INFORMATION: Xaa at position 6 is Phe or Cys
<220> FEATURE:
<221> NAME/KEY: MISC_FEATURE
<222> LOCATION: (10)..(10)
<223> OTHER INFORMATION: Xaa at position 10 is Val or Cys
<220> FEATURE:
<221> NAME/KEY: MISC_FEATURE
<222> LOCATION: (16)..(16)
<223> OTHER INFORMATION: Xaa at position 16 is Gly or Cys
<220> FEATURE:
<221> NAME/KEY: MISC_FEATURE
<222> LOCATION: (17)..(17)
<223> OTHER INFORMATION: Xaa at position 17 is Gln or Cys
<220> FEATURE:
<221> NAME/KEY: MISC_FEATURE
<222> LOCATION: (18)..(18)
<223> OTHER INFORMATION: Xaa at position 18 is Ala or Cys
<220> FEATURE:
<221> NAME/KEY: MISC_FEATURE
<222> LOCATION: (19)..(19)
<223> OTHER INFORMATION: Xaa at position 19 is Ala or Cys
<220> FEATURE:
<221> NAME/KEY: MISC_FEATURE
<222> LOCATION: (20)..(20)
<223> OTHER INFORMATION: Xaa at position 20 is Lys or Cys
<220> FEATURE:
<221> NAME/KEY: MISC_FEATURE
<222> LOCATION: (21)..(21)
<223> OTHER INFORMATION: Xaa at position 21 is Glu or Cys
<220> FEATURE:
<221> NAME/KEY: MISC_FEATURE
<222> LOCATION: (24)..(24)
<223> OTHER INFORMATION: Xaa at position 24 is Ala or Cys
<220> FEATURE:
<221> NAME/KEY: MISC_FEATURE
<222> LOCATION: (28)..(28)
<223> OTHER INFORMATION: Xaa at position 28 is Lys or Cys
<220> FEATURE:
<221> NAME/KEY: MISC_FEATURE
<222> LOCATION: (29)..(29)
<223> OTHER INFORMATION: Xaa at position 29 is Gly or Cys
<220> FEATURE:
<221> NAME/KEY: MISC_FEATURE
<222> LOCATION: (30)..(30)
<223> OTHER INFORMATION: Xaa at position 30 is Gly or Cys
<220> FEATURE:
<221> NAME/KEY: MISC_FEATURE
<222> LOCATION: (31)..(31)
<223> OTHER INFORMATION: Xaa at position 31 is Pro or Cys
<220> FEATURE:
<221> NAME/KEY: MISC_FEATURE
<222> LOCATION: (32)..(32)
<223> OTHER INFORMATION: Xaa at position 32 is Ser, Pro, His or Cys
<220> FEATURE:
<221> NAME/KEY: MISC_FEATURE
<222> LOCATION: (33)..(33)
<223> OTHER INFORMATION: Xaa at position 33 is Ser, Arg, Thr, Trp, Lys,
      or Cys
<220> FEATURE:
```

```
<221> NAME/KEY: MISC_FEATURE
<222> LOCATION: (34)..(34)
<223> OTHER INFORMATION: Xaa at position 34 is Ser, Gly, or Cys
<220> FEATURE:
<221> NAME/KEY: MISC_FEATURE
<222> LOCATION: (35)..(35)
<223> OTHER INFORMATION: Xaa at position 35 is Ala, Asp, Arg, Glu, Lys,
      Gly or Cys
<220> FEATURE:
<221> NAME/KEY: MISC_FEATURE
<222> LOCATION: (36)..(36)
<223> OTHER INFORMATION: Xaa at position 36 is Pro, Ala, Cys, Absent, or
      a Modified
      Residue
<220> FEATURE:
<221> NAME/KEY: MOD_RES
<222> LOCATION: (36)..(36)
<223> OTHER INFORMATION: AMIDATION
<220> FEATURE:
<221> NAME/KEY: MISC_FEATURE
<222> LOCATION: (37)..(37)
<223> OTHER INFORMATION: Xaa at position 37 is Pro, Ala, Cys, Absent, or
      a Modified
      Residue
<220> FEATURE:
<221> NAME/KEY: MOD_RES
<222> LOCATION: (37)..(37)
<223> OTHER INFORMATION: AMIDATION
<220> FEATURE:
<221> NAME/KEY: MISC_FEATURE
<222> LOCATION: (38)..(38)
<223> OTHER INFORMATION: Xaa at position 38 is Pro, Ala, Arg, Lys, His,
      Cys, Absent, or a
      Modified Residue
<220> FEATURE:
<221> NAME/KEY: MOD_RES
<222> LOCATION: (38)..(38)
<223> OTHER INFORMATION: AMIDATION
<220> FEATURE:
<221> NAME/KEY: MISC_FEATURE
<222> LOCATION: (39)..(39)
<223> OTHER INFORMATION: Xaa at position 39 is Ser, His, Pro, Lys, Arg,
      Gly, Cys, Absent,
      or a Modified Residue
<220> FEATURE:
<221> NAME/KEY: MOD_RES
<222> LOCATION: (39)..(39)
<223> OTHER INFORMATION: AMIDATION
<220> FEATURE:
<221> NAME/KEY: MISC_FEATURE
<222> LOCATION: (40)..(40)
<223> OTHER INFORMATION: Xaa at position 40 is His, Ser, Arg, Lys, Pro,
      Gly, Cys, Absent,
      or a Modified Residue
<220> FEATURE:
<221> NAME/KEY: MOD_RES
<222> LOCATION: (40)..(40)
<223> OTHER INFORMATION: AMIDATION
<220> FEATURE:
<221> NAME/KEY: MISC_FEATURE
<222> LOCATION: (41)..(41)
<223> OTHER INFORMATION: Xaa at position 41 is His, Ser, Arg, Lys, Cys,
      Absent, or a
      Modified Residue
<220> FEATURE:
<221> NAME/KEY: MOD_RES
<222> LOCATION: (41)..(41)
<223> OTHER INFORMATION: AMIDATION
<220> FEATURE:
<221> NAME/KEY: MISC_FEATURE
<222> LOCATION: (42)..(42)
<223> OTHER INFORMATION: Xaa at position 42 is Gly, His, Cys, Absent,
      or a Modified
      Residue
<220> FEATURE:
<221> NAME/KEY: MOD_RES
<222> LOCATION: (42)..(42)
<223> OTHER INFORMATION: AMIDATION
<220> FEATURE:
```

-continued

```
<221> NAME/KEY: MISC_FEATURE
<222> LOCATION: (43)..(43)
<223> OTHER INFORMATION: Xaa at position 43 is Pro, His, Cys, Absent, or
      a Modified
      Residue
<220> FEATURE:
<221> NAME/KEY: MOD_RES
<222> LOCATION: (43)..(43)
<223> OTHER INFORMATION: AMIDATION
<220> FEATURE:
<221> NAME/KEY: MISC_FEATURE
<222> LOCATION: (44)..(44)
<223> OTHER INFORMATION: Xaa at position 44 is Ser, His, Cys, Absent, or
      a Modified
      Residue
<220> FEATURE:
<221> NAME/KEY: MOD_RES
<222> LOCATION: (44)..(44)
<223> OTHER INFORMATION: AMIDATION

<400> SEQUENCE: 9

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Gly Pro Xaa
            20                  25                  30

Xaa Xaa Xaa Xaa Xaa Xaa Xaa Xaa Xaa Xaa Xaa Xaa
            35                  40

<210> SEQ ID NO 10
<211> LENGTH: 39
<212> TYPE: PRT
<213> ORGANISM: Artificial
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is L-histidine, D-histidine,
      desamino-histidine,
      2-amino-histidine, beta-hydroxy-histidine, homohistidine,
      alpha-fluoromethyl-histidine, alpha-methyl-histidine, Arg, Tyr,
<220> FEATURE:
<221> NAME/KEY: MISC_FEATURE
<222> LOCATION: (2)..(2)
<223> OTHER INFORMATION: Xaa at position 2 is Gly, Ser, Ala, or Thr
<220> FEATURE:
<221> NAME/KEY: MISC_FEATURE
<222> LOCATION: (3)..(3)
<223> OTHER INFORMATION: Xaa at position 3 is Glu, Ala, or Asp
<220> FEATURE:
<221> NAME/KEY: MISC_FEATURE
<222> LOCATION: (4)..(4)
<223> OTHER INFORMATION: Xaa at position 4 is Gly, Ala, or Val
<220> FEATURE:
<221> NAME/KEY: MISC_FEATURE
<222> LOCATION: (5)..(5)
<223> OTHER INFORMATION: Xaa at position 5 is Thr, Cys, or Ala
<220> FEATURE:
<221> NAME/KEY: MISC_FEATURE
<222> LOCATION: (6)..(6)
<223> OTHER INFORMATION: Xaa at position 6 is Phe, Cys, Ala, or Tyr
<220> FEATURE:
<221> NAME/KEY: MISC_FEATURE
<222> LOCATION: (7)..(7)
<223> OTHER INFORMATION: Xaa at position 7 is Thr or Ser
<220> FEATURE:
<221> NAME/KEY: MISC_FEATURE
<222> LOCATION: (8)..(8)
<223> OTHER INFORMATION: Xaa at position 8 is Ser, Ala, or Thr
<220> FEATURE:
<221> NAME/KEY: MISC_FEATURE
<222> LOCATION: (9)..(9)
<223> OTHER INFORMATION: Xaa at position 9 is Asp or Glu
<220> FEATURE:
<221> NAME/KEY: MISC_FEATURE
```

```
<222> LOCATION: (10)..(10)
<223> OTHER INFORMATION: Xaa at position 10 is Leu, Cys, Ala, Ile, Val,
      or Met
<220> FEATURE:
<221> NAME/KEY: MISC_FEATURE
<222> LOCATION: (11)..(11)
<223> OTHER INFORMATION: Xaa at position 11 is Ser or Ala
<220> FEATURE:
<221> NAME/KEY: MISC_FEATURE
<222> LOCATION: (12)..(12)
<223> OTHER INFORMATION: Xaa at position 12 is Lys or Ala
<220> FEATURE:
<221> NAME/KEY: MISC_FEATURE
<222> LOCATION: (13)..(13)
<223> OTHER INFORMATION: Xaa at position 13 is Gln or Ala
<220> FEATURE:
<221> NAME/KEY: MISC_FEATURE
<222> LOCATION: (14)..(14)
<223> OTHER INFORMATION: Xaa at position 14 is Met, Ala, Leu, Ile, or
      Val
<220> FEATURE:
<221> NAME/KEY: MISC_FEATURE
<222> LOCATION: (15)..(15)
<223> OTHER INFORMATION: Xaa at position 15 is Glu or Ala
<220> FEATURE:
<221> NAME/KEY: MISC_FEATURE
<222> LOCATION: (16)..(16)
<223> OTHER INFORMATION: Xaa at position 16 is Glu, Cys, or Ala
<220> FEATURE:
<221> NAME/KEY: MISC_FEATURE
<222> LOCATION: (17)..(17)
<223> OTHER INFORMATION: Xaa at position 17 is Glu, Cys, or Ala
<220> FEATURE:
<221> NAME/KEY: MISC_FEATURE
<222> LOCATION: (18)..(18)
<223> OTHER INFORMATION: Xaa at position 18 is Ala or Cys
<220> FEATURE:
<221> NAME/KEY: MISC_FEATURE
<222> LOCATION: (19)..(19)
<223> OTHER INFORMATION: Xaa at position 19 is Val, Cys, or Ala
<220> FEATURE:
<221> NAME/KEY: MISC_FEATURE
<222> LOCATION: (20)..(20)
<223> OTHER INFORMATION: Xaa at position 20 is Arg, Cys, or Ala
<220> FEATURE:
<221> NAME/KEY: MISC_FEATURE
<222> LOCATION: (21)..(21)
<223> OTHER INFORMATION: Xaa at position 21 is Leu, Cys, or Ala
<220> FEATURE:
<221> NAME/KEY: MISC_FEATURE
<222> LOCATION: (22)..(22)
<223> OTHER INFORMATION: Xaa at position 22 is Phe, Ala, or Tyr
<220> FEATURE:
<221> NAME/KEY: MISC_FEATURE
<222> LOCATION: (23)..(23)
<223> OTHER INFORMATION: Xaa at position 23 is Ile, Val, Leu, Gly, or
      Met
<220> FEATURE:
<221> NAME/KEY: MISC_FEATURE
<222> LOCATION: (24)..(24)
<223> OTHER INFORMATION: Xaa at position 24 is Glu, Cys, Ala, or Asp
<220> FEATURE:
<221> NAME/KEY: MISC_FEATURE
<222> LOCATION: (25)..(25)
<223> OTHER INFORMATION: Xaa at position 25 is Trp, Ala, Phe, or Tyr
<220> FEATURE:
<221> NAME/KEY: MISC_FEATURE
<222> LOCATION: (26)..(26)
<223> OTHER INFORMATION: Xaa at position 26 is Leu or Ala
<220> FEATURE:
<221> NAME/KEY: MISC_FEATURE
<222> LOCATION: (27)..(27)
<223> OTHER INFORMATION: Xaa at position 27 is Lys or Ala
<220> FEATURE:
<221> NAME/KEY: MISC_FEATURE
<222> LOCATION: (28)..(28)
<223> OTHER INFORMATION: Xaa at position 28 is Asn, Cys, or Ala
<220> FEATURE:
<221> NAME/KEY: MISC_FEATURE
```

```
<222> LOCATION: (29)..(29)
<223> OTHER INFORMATION: Xaa at position 29 is Gly or Cys
<220> FEATURE:
<221> NAME/KEY: MISC_FEATURE
<222> LOCATION: (30)..(30)
<223> OTHER INFORMATION: Xaa at position 30 is Gly or Cys
<220> FEATURE:
<221> NAME/KEY: MISC_FEATURE
<222> LOCATION: (31)..(31)
<223> OTHER INFORMATION: Xaa at position 31 is Pro or Cys
<220> FEATURE:
<221> NAME/KEY: MISC_FEATURE
<222> LOCATION: (32)..(32)
<223> OTHER INFORMATION: Xaa at position 32 is Ser, Cys, Absent, or a
      Modified Residue
<220> FEATURE:
<221> NAME/KEY: MOD_RES
<222> LOCATION: (32)..(32)
<223> OTHER INFORMATION: AMIDATION
<220> FEATURE:
<221> NAME/KEY: MISC_FEATURE
<222> LOCATION: (33)..(33)
<223> OTHER INFORMATION: Xaa at position 33 is Ser, Cys, Absent, or a
      Modified Residue
<220> FEATURE:
<221> NAME/KEY: MOD_RES
<222> LOCATION: (33)..(33)
<223> OTHER INFORMATION: AMIDATION
<220> FEATURE:
<221> NAME/KEY: MISC_FEATURE
<222> LOCATION: (34)..(34)
<223> OTHER INFORMATION: Xaa at position 34 is Gly, Cys, Absent, or a
      Modified Residue
<220> FEATURE:
<221> NAME/KEY: MOD_RES
<222> LOCATION: (34)..(34)
<223> OTHER INFORMATION: AMIDATION
<220> FEATURE:
<221> NAME/KEY: MISC_FEATURE
<222> LOCATION: (35)..(35)
<223> OTHER INFORMATION: Xaa at position 35 is Ala, Cys, Absent, or a
      Modified Residue
<220> FEATURE:
<221> NAME/KEY: MOD_RES
<222> LOCATION: (35)..(35)
<223> OTHER INFORMATION: AMIDATION
<220> FEATURE:
<221> NAME/KEY: MISC_FEATURE
<222> LOCATION: (36)..(36)
<223> OTHER INFORMATION: Xaa at position 36 is Pro, Cys, Absent, or a
      Modified Residue
<220> FEATURE:
<221> NAME/KEY: MOD_RES
<222> LOCATION: (36)..(36)
<223> OTHER INFORMATION: AMIDATION
<220> FEATURE:
<221> NAME/KEY: MISC_FEATURE
<222> LOCATION: (37)..(37)
<223> OTHER INFORMATION: Xaa at position 37 is Pro, Cys, Absent, or a
      Modified Residue
<220> FEATURE:
<221> NAME/KEY: MOD_RES
<222> LOCATION: (37)..(37)
<223> OTHER INFORMATION: AMIDATION
<220> FEATURE:
<221> NAME/KEY: MISC_FEATURE
<222> LOCATION: (38)..(38)
<223> OTHER INFORMATION: Xaa at position 38 is Pro, Cys, Absent, or a
      Modified Residue
<220> FEATURE:
<221> NAME/KEY: MOD_RES
<222> LOCATION: (38)..(38)
<223> OTHER INFORMATION: AMIDATION
<220> FEATURE:
<221> NAME/KEY: MISC_FEATURE
<222> LOCATION: (39)..(39)
<223> OTHER INFORMATION: Xaa at position 39 is Ser, Cys, Absent, or a
      Modified Residue
<220> FEATURE:
```

```
-continued

<221> NAME/KEY: MOD_RES
<222> LOCATION: (39)..(39)
<223> OTHER INFORMATION: AMIDATION

<400> SEQUENCE: 10

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa
        35
```